(12) United States Patent
Wang et al.

(10) Patent No.: US 11,583,302 B2
(45) Date of Patent: Feb. 21, 2023

(54) THROMBECTOMY DEVICE SYSTEM

(71) Applicant: SHANGHAI HEARTCARE MEDICAL TECHNOLOGY CO., LTD., Shanghai (CN)

(72) Inventors: Guohui Wang, Shanghai (CN); Zhen Wang, Shanghai (CN); Jianping Wu, Shanghai (CN); Zongyu Xue, Shanghai (CN)

(73) Assignee: SHANGHAI HEARTCARE MEDICAL TECHNOLOGY CO., LTD., Shanghai (CN)

( * ) Notice: Subject to any disclaimer, the term of this patent is extended or adjusted under 35 U.S.C. 154(b) by 150 days.

(21) Appl. No.: 16/492,762

(22) PCT Filed: Mar. 9, 2018

(86) PCT No.: PCT/CN2018/078570
§ 371 (c)(1),
(2) Date: Sep. 10, 2019

(87) PCT Pub. No.: WO2018/161959
PCT Pub. Date: Sep. 13, 2018

(65) Prior Publication Data
US 2021/0137541 A1 May 13, 2021

(30) Foreign Application Priority Data

Mar. 10, 2017 (CN) .......................... 201710142837.3
Mar. 29, 2017 (CN) .......................... 201710198720.7
Jul. 14, 2017 (CN) .......................... 201710575843.8

(51) Int. Cl.
*A61B 17/221* (2006.01)
*A61B 17/00* (2006.01)

(52) U.S. Cl.
CPC .. *A61B 17/221* (2013.01); *A61B 2017/00867* (2013.01); *A61B 2017/2215* (2013.01)

(58) Field of Classification Search
CPC .......... A61B 17/221; A61B 17/320725; A61B 17/22; A61B 2017/2215;
(Continued)

(56) References Cited

U.S. PATENT DOCUMENTS

| 5,855,600 A * | 1/1999 | Alt .......................... A61F 2/915 |
| | | 623/1.15 |
| 6,096,072 A * | 8/2000 | Kanesaka ............... A61F 2/915 |
| | | 623/1.15 |

(Continued)

FOREIGN PATENT DOCUMENTS

| CN | 103841905 A | 6/2014 |
| CN | 104586469 A | 5/2015 |

(Continued)

OTHER PUBLICATIONS

PCT; App No. PCT/CN2018/078570; International Search Report and Written Opinion dated Jun. 1, 2018.

*Primary Examiner* — Jocelin C Tanner
(74) *Attorney, Agent, or Firm* — Fitch, Even, Tabin & Flannery LLP

(57) ABSTRACT

Disclosed is a thrombectomy stent system, comprising a thrombectomy stent, wherein the thrombectomy stent is roll-shaped, and the cross section of the thrombectomy stent is of an open-ring structure. Disclosed is a thrombectomy device, comprising the thrombectomy stent, wherein the thrombectomy stent is provided with a developing element that can accurately display the expansion state of the thrombectomy stent during thrombectomy and the specific position of the thrombectomy stent so as to determine the situation of the thrombectomy stent being fused with a blood vessel. Disclosed is a thrombectomy device system, com- (Continued)

prising the thrombectomy stent and a push rod, wherein a proximal end of the thrombectomy stent is connected to the push rod, and the proximal end of the thrombectomy stent or the push rod is connected to a catching member; and the catching member is configured to receive the thrombectomy stent. The catching member can effectively catch a thrombus that is detached during the thrombectomy.

34 Claims, 11 Drawing Sheets

(58) Field of Classification Search
CPC .......... A61B 2017/00867; A61F 2/013; A61F 2/0105; A61F 2/0108; A61F 2002/016; A61F 2002/018
See application file for complete search history.

(56) References Cited

U.S. PATENT DOCUMENTS

| | | | |
|---|---|---|---|
| 9,358,094 B2* | 6/2016 | Martin | A61B 17/22031 |
| 10,070,878 B2* | 9/2018 | Ma | A61B 17/221 |
| 10,092,309 B1* | 10/2018 | Shinsky | A61B 17/221 |
| 2007/0112372 A1 | 5/2007 | Sosnowski | |
| 2007/0288054 A1* | 12/2007 | Tanaka | A61B 17/221 606/200 |
| 2011/0009950 A1* | 1/2011 | Grandfield | A61F 2/91 623/1.16 |
| 2011/0160763 A1* | 6/2011 | Ferrera | A61F 2/82 606/200 |
| 2011/0224707 A1* | 9/2011 | Miloslavski | A61B 17/221 606/159 |
| 2015/0112376 A1* | 4/2015 | Molaei | A61B 17/22031 606/200 |
| 2015/0209165 A1* | 7/2015 | Grandfield | A61F 2/915 623/1.2 |
| 2017/0079766 A1* | 3/2017 | Wang | A61B 17/221 |
| 2017/0231742 A1* | 8/2017 | Epstein | A61B 34/20 606/200 |
| 2018/0325536 A1* | 11/2018 | Deen | A61B 17/221 |

FOREIGN PATENT DOCUMENTS

| | | |
|---|---|---|
| CN | 105354811 A | 2/2016 |
| CN | 105662534 A | 6/2016 |
| CN | 105726088 A | 7/2016 |
| CN | 106859729 A | 6/2017 |
| CN | 106963451 A | 7/2017 |
| WO | 2006116636 A1 | 11/2006 |

* cited by examiner

THROMBECTOMY DEVICE SYSTEM

CROSS-REFERENCE TO RELATED APPLICATION

This application is a U.S. national phase application of International Application No. PCT/CN2018/078570, filed Mar. 9, 2018, which claims priority to Chinese Application No. 201710575843.8, filed Jul. 14, 2017, to Chinese Application No. 201710198720.7, filed Mar. 29, 2017, and to Chinese Application No. 201710142837.3, filed Mar. 10, 2017.

TECHNICAL FIELD

The present invention belongs to the field of medical instruments, and in particular relates to a thrombectomy device system.

BACKGROUND ART

Stroke is one of the most common diseases in the world at present, and has the characteristics of high incidence, high morbidity and high disability. The annual incidence of cerebrovascular diseases in China is 219/100,000 in cities and 185/100,000 in rural areas and is still rising year by year. The morbidity of cerebrovascular diseases increased from 5.9‰ to 9.7‰ from 1998 to 2008. About three quarters of living patients suffering from cerebrovascular diseases are disabled to work on different levels. It was reported that 80% of stroke patients suffer from different levels of limb dysfunctions, and 43.7% cannot take care of themselves. Intravenous rt-PA thrombolysis is currently the only effective therapeutic method for acute cerebral infarction confirmed by evidence-based medicine. However, the intravenous thrombolysis requires a long treatment time, has great damage to ischemic brain tissues, is accompanied by bleeding risk, and is very low in recanalization rate. The recanalization rate of basilar artery thrombolysis is only about 30%, the recanalization rate of pathological thrombolysis at the terminal of carotid artery is only 6%, and the recanalization rate of thrombolysis in common carotid artery is only about 27%. Moreover, the time window for intravenous thrombolysis is only about 4 hours. It can be seen from the above that the single intravenous thrombolysis is far from enough for cerebral artery occlusion, and the single intravenous thrombolysis may be insufficient to meet actual clinical needs.

A thrombectomy device is a medical tool for catching a thrombus in a blood vessel. The thrombectomy device is introduced to the position of embolism through a microcatheter system, is released to catch the thrombus at the position of embolism, and then is withdrawn through the microcatheter to take out the thrombus. However, the existing thrombectomy devices are mainly for large blood vessels and cannot enter small cerebral arteries. Moreover, if the thrombectomy stent itself is improperly designed, irreversible damage is easily caused to the blood vessel, resulting in other complications such as restenosis and vascular rupture. In addition, the thrombus is easy to be detached during catching, resulting in long time consumption and low vascular recanalization rate. If it takes a long time, the ischemia time will be too long, which is easy to cause irreversible damage to the brain. Poor development of the thrombectomy stent may also cause the problems such as excessive thrombectomy time, thrombus detachment and poor thrombolysis effect. All of these are the problems that has to be faced in the application of thrombectomy devices to the treatment of stroke caused by cerebral thrombosis.

SUMMARY OF THE INVENTION

In view of the deficiencies of the prior art, the inventors have studied to obtain a thrombectomy stent system, comprising a thrombectomy stent, wherein the thrombectomy stent is roll-shaped; and the cross section of the thrombectomy stent is of an open-ring structure. The outer diameter of the thrombectomy stent varies with the degree of curling of the thrombectomy stent. The open-ring roll-shaped design facilitates the adjustment of curling tightness as needed so as to adjust the outer diameter of the thrombectomy stent to adapt to the size of different blood vessels and adapt to different support forces. When a blood vessel is small, the degree of curling is increased, and the outer diameter is reduced; and vice versa. A suitable support force is beneficial to improving the fusion of the thrombectomy stent and a thrombus without damaging the blood vessel and to increasing the capability of catching the thrombus. The support force here refers to a tension of the thrombectomy stent against an inner wall of the blood vessel at the operation site.

Further, both a distal end and a proximal end of the thrombectomy stent are in an open state. During thrombectomy, the middle segment of the thrombectomy stent is often fused with a thrombus, and at this time the middle segment of the thrombectomy stent is often deformed so that the outer diameter of the segment is reduced. If the distal end and/or the proximal end of the thrombectomy stent is/are in a closed state, the outer diameter of the entire thrombectomy stent is reduced during thrombectomy, so that the thrombus is easy to be detached from the thrombectomy stent during thrombectomy due to the resistance of the vascular wall. If both the distal end and the proximal end of the thrombectomy stent are in the open state, the outer diameter of the middle segment (the thrombectomy part) of the thrombectomy stent is reduced, and the outer diameters of two ends of the thrombectomy stent are greater than that of the middle segment, at this time the stent is dumbbell-shaped, so that the thrombus is not easy to be detached from the stent during thrombectomy. Therefore, the thrombectomy stent in the state of being open at both ends is obviously better, in thrombus fusion and catching ability, i.e., in thrombectomy effect, than the thrombectomy stent in the state of being closed at one or both ends.

Further, the closer to the most distal end of the thrombectomy stent is, the smaller the perimeter of the cross section of the distal end of the thrombectomy stent.

Further, the closer to the most proximal end of the thrombectomy stent is, the smaller the perimeter of the cross section of the proximal end of the thrombectomy stent.

Further, the cross section of the most proximal end of the thrombectomy stent is reduced to a dot.

Further, the cross section of the distal end of the thrombectomy stent is C-shaped.

Further, the cross section of the proximal end of the thrombectomy stent is C-shaped.

Further, the thrombectomy stent comprises a plurality of identical or different grid cells.

Further, the grid cells are connected to each other in a mesh shape.

In one specific embodiment, the meshes in the middle are larger than the meshes on both sides and are stronger in support force, so that the thrombectomy stent can be better embedded into the thrombus.

In one specific embodiment, the shape of the grid cells includes one or more of a pattern composed of arcs and a pattern composed of polygons, arcs and straight lines.

In another specific embodiment, the shape of the grid cells includes one or more of a circle, an ellipse, a quadrangle, a triangle, a diamond and a trapezoid.

In still another specific embodiment, the shape of the grid cells includes a pattern composed of a plurality of arcs.

Further, the thrombectomy stent has a first state and a second state; and in the second state, the shape of the grid cells changes so that the outer diameter of the middle segment of the thrombectomy stent is less than the outer diameters of two ends thereof.

Further, in the first state, the shape of the grid cells is stable.

Further, in the first state, the width of grid wires of the grid cells is 0.05 mm to 0.16 mm; and the size of the grid cells are 3 mm to 5 mm. Preferably, the width of the grid wires of the grid cells is 0.07 mm to 0.14 mm. The size of the grid cells are 3.6 mm to 4.5 mm. The support force of the thrombectomy stent against the operation site is determined by the width and thickness of the grid wires of the grid cells, the size of the grid cells and the roll-shaped open-ring structure of the thrombectomy stent together, where the roll-shaped open-ring structure can facilitate the adjustment of the support force. In the present invention, the thickness of the grid wires of the grid cells is as shown in the prior art. The thrombectomy stent is designed to have different outer diameters and lengths to adapt to cerebral vessels of different diameters and thrombi of different lengths.

Further, developing elements are disposed at ends of the grid cells at the distal end of the thrombectomy stent. The developing elements are used for positioning the thrombectomy stent in the blood vessel during surgery.

Further, the distal end of the thrombectomy stent is provided with developing elements which extend along the distal end of the thrombectomy stent. Preferably, the number of the developing elements at the ends of the grid cells at the distal end of the thrombectomy stent is 2-8. Preferably, the number is 4. The raised developing elements facilitate the thrombectomy stent to pass through the thrombus site.

Further, the material of the thrombectomy stent includes a memory alloy. Further, the material of the thrombectomy stent includes a nickel-titanium alloy and/or a cobalt-based alloy.

Further, the thrombectomy stent system further comprises a push rod; developing elements are disposed at the distal end of the thrombectomy stent; and the proximal end of the thrombectomy stent is connected to a distal end of the push rod, and a developing element is disposed at the junction. Further, the developing element uses noble metal developing points and has strong developing performance, which can help a surgeon determine the position of the thrombectomy stent during surgery.

In one specific embodiment, the developing element at the junction of the proximal end of the thrombectomy stent and the distal end of the push rod is a developing ring; the developing ring is sheathed at the junction.

In another specific embodiment, the proximal end of the thrombectomy stent is connected to the distal end of push rod by means of soldering, sleeve connection, linking or adhesive fixed connection. Preferably, the soldering includes silver soldering and/or gold soldering.

In still another specific embodiment, the proximal end of the thrombectomy stent is connected to the distal end of the push rod by means of soldering, sleeve connection or linking first and then adhesive fixed connection.

Further, the adhesive includes a UV adhesive and/or an epoxy resin adhesive.

Further, the material of the push rod includes a nickel-titanium alloy. Therefore, the push rod has good flexibility and resilience, which is convenient for pushing the thrombectomy stent system in the tortuous blood vessel.

Further, the distal end of the push rod is configured in a tapered step shape to provide a smooth transition when connected to the proximal end of the thrombectomy stent.

Further, the outer surface of the push rod is coated with a polymer material with a low friction coefficient. It facilitates reducing the friction of the push rod to provide a high push performance. The polymer material with a low friction coefficient includes PTFE (polytetrafluoroethylene) and/or PET (polyethylene terephthalate plastic).

Further, the thrombectomy stent system further comprises an introducing sheath; and the introducing sheath is a double-layer tube, the material of the inner-layer tube including PTFE or/and HDPE (high density polyethylene), and the material of the outer-layer tube including nylon and/or Pebax (nylon elastomer). The introducing sheath serves to introduce the thrombectomy stent into a microcatheter along with the push rod. The microcatheter is a surgical accessory.

Further, an inner wall of a distal end of the inner-layer tube is configured to have smooth rounded transition.

Further, a handle is disposed at a proximal end of the introducing sheath.

In view of the deficiencies of the prior art, particularly the design problem of developing elements on a thrombectomy stent, the present invention further provides a thrombectomy device, comprising a thrombectomy stent, wherein developing elements are disposed on the thrombectomy stent. The shape of the developing elements may be set as needed, and may be, for example, line-shaped, ring-shaped, mesh-shaped and/or dot-shaped.

Further, the developing elements are disposed at both a distal end and a proximal end of the thrombectomy stent. In the present invention, the distal end refers to the end far away from an operator (such as a surgeon); and the proximal end refers to the end close to the operator (such as the surgeon).

Further, the thrombectomy stent is roll-shaped; the cross section of the thrombectomy stent is of an open-ring structure. The outer diameter of the thrombectomy stent varies with the degree of curling of the thrombectomy stent. The open-ring roll-shaped design facilitates the adjustment of curling tightness as needed so as to adjust the outer diameter of the thrombectomy stent to adapt to the size of different blood vessels and adapt to different support forces. When a blood vessel is small, the degree of curling is increased, and the outer diameter is reduced; and vice versa. A suitable support force is beneficial to improving the fusion of the thrombectomy stent and a thrombus without damaging the blood vessel and to increasing the capability of catching the thrombus. The support force here refers to a tension of the thrombectomy stent against an inner wall of the blood vessel at the operation site.

Further, the number of the developing elements is greater than or equal to 2, and the developing elements are uniformly distributed around the roll-shaped circumference of the thrombectomy stent.

Preferably, the number of the developing elements is greater than or equal to 3.

Further, the number of the developing elements at the distal end of the thrombectomy stent is greater than or equal to 2 (preferably greater than or equal to 3), and the developing elements at the distal end of the thrombectomy stent are uniformly distributed at the distal end of the thrombectomy stent; and the number of the developing elements at the proximal end of the thrombectomy stent is greater than or equal to 2 (preferably greater than or equal to 3), and the developing elements at the proximal end of the thrombectomy stent are uniformly distributed at the proximal end of the thrombectomy stent.

In one specific embodiment, the thrombectomy stent is roll-shaped; the cross section of the thrombectomy stent is of an open-ring structure; the number of the developing elements at the distal end of the thrombectomy stent is greater than or equal to 2 (preferably greater than or equal to 3), and the developing elements at the distal end of the thrombectomy stent are uniformly distributed at the distal end of the thrombectomy stent around the roll-shaped circumference of the thrombectomy stent; and the number of the developing elements at the proximal end of the thrombectomy stent is greater than or equal to 2 (preferably greater than or equal to 3), and the developing elements at the proximal end of the thrombectomy stent are uniformly distributed at the proximal end of the thrombectomy stent around the roll-shaped circumference of the thrombectomy stent.

Further, developing elements are disposed at a middle segment of the thrombectomy stent. In the present invention, the middle segment of the thrombectomy stent refers to a segment between the distal end and the proximal end of the thrombectomy stent.

Further, the number of the developing elements at the distal end of the thrombectomy stent is greater than or equal to 2 (preferably greater than or equal to 3), and the developing elements at the distal end of the thrombectomy stent are uniformly distributed at the distal end of the thrombectomy stent; the number of the developing elements at the proximal end of the thrombectomy stent is greater than or equal to 2 (preferably greater than or equal to 3), and the developing elements at the proximal end of the thrombectomy stent are uniformly distributed at the proximal end of the thrombectomy stent; and the number of the developing elements at the middle segment of the thrombectomy stent is greater than or equal to 2 (preferably greater than or equal to 3), and the developing elements at the middle segment of the thrombectomy stent are uniformly distributed at the middle segment of the thrombectomy stent.

In one specific embodiment, the thrombectomy stent is roll-shaped; the cross section of the thrombectomy stent is of an open-ring structure; the number of the developing elements at the distal end of the thrombectomy stent is greater than or equal to 2 (preferably greater than or equal to 3), and the developing elements at the distal end of the thrombectomy stent are uniformly distributed at the distal end of the thrombectomy stent around the roll-shaped circumference of the thrombectomy stent; the number of the developing elements at the proximal end of the thrombectomy stent is greater than or equal to 2 (preferably greater than or equal to 3), and the developing elements at the proximal end of the thrombectomy stent are uniformly distributed at the proximal end of the thrombectomy stent around the roll-shaped circumference of the thrombectomy stent; and the number of the developing elements at the middle segment of the thrombectomy stent is greater than or equal to 2 (preferably greater than or equal to 3), and the developing elements at the middle segment of the thrombectomy stent are uniformly distributed at the middle segment of the thrombectomy stent around the roll-shaped circumference of the thrombectomy stent.

In another specific embodiment, the developing elements include line-shaped developing lines.

Further, one end of the developing line is disposed at the distal end or a distal end face of the thrombectomy stent, and the other end thereof is disposed at the proximal end or a proximal end face of the thrombectomy stent.

Further, the number of the developing lines is greater than or equal to 3, and the developing lines are uniformly arranged on the thrombectomy stent.

In one specific embodiment, the thrombectomy stent is roll-shaped; the cross section of the thrombectomy stent is of an open-ring structure; and the number of the developing lines is greater than or equal to 3, and the developing lines extend in the axial direction of the thrombectomy stent and are uniformly arranged on the thrombectomy stent around the roll-shaped circumference of the thrombectomy stent.

In another specific embodiment, the thrombectomy stent is roll-shaped; the cross section of the thrombectomy stent is of an open-ring structure; the thrombectomy stent is roll-shaped; and the developing lines extend in the direction of the roll-shaped circumference of the thrombectomy stent.

In still another specific embodiment, the thrombectomy stent is roll-shaped; the cross section of the thrombectomy stent is of an open-ring structure; and the developing lines not only axially extend along the thrombectomy stent but also extend back and forth in the direction of the roll-shaped circumference of the thrombectomy stent.

Further, the number of the developing lines is greater than or equal to 3, and the developing lines are uniformly arranged on the thrombectomy stent around the roll-shaped circumference of the thrombectomy stent.

Further, the developing elements are disposed in a manner including one or more of spraying or brushing a developing material to the thrombectomy stent or mounting the developing elements onto the thrombectomy stent by means of winding, buckling, perforating, soldering or bonding.

In one specific embodiment, the entire thrombectomy stent is covered with a developing material. Covering with a developing material comprises spraying or brushing the developing material to the thrombectomy stent.

In another specific embodiment, the developing elements include a mesh-shaped developing mesh; and the developing mesh is located at the most distal end of the thrombectomy stent to close an opening at the distal end of the thrombectomy stent.

Further, the distal end of the thrombectomy stent is in an open state. During thrombectomy, the middle segment of the thrombectomy stent is often fused with a thrombus, and at this time the middle segment of the thrombectomy stent is often deformed so that the outer diameter of the segment is reduced. If the distal end of the thrombectomy stent is in a closed state, both the outer diameters of the middle segment and the distal end of the thrombectomy stent are reduced during thrombectomy, so that the thrombus is easy to be detached from the thrombectomy stent during thrombectomy due to the resistance of the vascular wall. If the distal end of the thrombectomy stent is in the open state, the outer diameter of the middle segment (the thrombectomy part) of the thrombectomy stent is reduced, and the outer diameters of two ends of the thrombectomy stent are greater than that of the middle segment, and at this time the thrombectomy stent is dumbbell-shaped, and especially the outer diameter of the distal end of the thrombectomy stent is greater than that of the middle segment of the thrombectomy stent, so that the thrombus is not easy to be detached from the stent during thrombectomy. Therefore, the thrombectomy stent in the state of being open at the distal end is obviously better, in thrombus fusion and catching ability, i.e., in thrombectomy effect, than the thrombectomy stent in the state of being closed at the distal end.

Further, the proximal end of the thrombectomy stent is in an open state. The outer diameter of the proximal end is greater than that of the middle segment of the thrombectomy stent during thrombectomy, so that the thrombus is not easy to be detached from the proximal end.

Further, the closer to the most distal end of the thrombectomy stent is, the smaller the perimeter of the cross section of the distal end of the thrombectomy stent. It facilitates the distal end of the thrombectomy stent to be curled to be smaller so as to extend into a smaller blood vessel, which expands the range of application of the thrombectomy stent.

Further, the closer to the most proximal end of the thrombectomy stent is, the smaller the perimeter of the cross section of the proximal end of the thrombectomy stent. It facilitates the thrombectomy stent to be better collapsed into the introducing sheath.

Further, the cross section of the most proximal end of the thrombectomy stent is reduced to a dot.

Further, the cross section of the distal end of the thrombectomy stent is C-shaped.

Further, the cross section of the proximal end of the thrombectomy stent is C-shaped.

Further, the thrombectomy stent comprises a plurality of identical or different grid cells.

Further, the grid cells are connected to each other in a mesh shape.

Further, the developing elements include a developing mesh; the developing mesh is located at the most distal end of the thrombectomy stent to close an opening at the distal end of the thrombectomy stent; and the grid size of the developing mesh is less than that of the grid cells. Therefore, during thrombectomy, it can not only display the position of the distal end of the thrombectomy stent but also catch the detached thrombus during thrombectomy.

In one specific embodiment, the shape of the grid cells includes one or more of a pattern composed of arcs and a pattern composed of polygons, arcs and straight lines.

In another specific embodiment, the shape of the grid cells includes one or more of a circle, an ellipse, a quadrangle, a triangle, a diamond and a trapezoid.

In still another specific embodiment, the shape of the grid cells includes a pattern composed of a plurality of arcs.

Further, the plurality of grid cells are sequentially arranged in rows, and the grid cells of two adjacent rows are arranged in a staggered manner. Preferably, the rows are parallel to the axial direction of the thrombectomy stent. That is, in a direction perpendicular to the axial direction of the thrombectomy stent, the grid cells of one of two adjacent rows align to gaps of every two adjacent grid cells of the other row. With such a design, the thrombectomy stent is more collapsible and more adaptable to small blood vessels and is easier to be collected into the introducing sheath.

Further, the grid cell is enclosed by four of the grid cells adjacent to each other.

Further, the grid cells include first grid cells and second grid cells; the first grid cell is enclosed by four of the second grid cells adjacent to each other; and the second grid cell is enclosed by four of the first grid cells adjacent to each other.

Further, the grid cells include first grid cells and second grid cells; a plurality of first grid cells are sequentially arranged in first grid cell rows which are parallel to the axial direction of the thrombectomy stent; a plurality of second grid cells are sequentially arranged in second grid cell rows which are parallel to the axial direction of the thrombectomy stent; and the first grid cell rows and the second grid cell rows are alternately arranged in the axial direction of the thrombectomy stent and arranged in a staggered manner in a direction perpendicular to the axial direction of the thrombectomy stent. The arrangement is as follows: the odd-numbered rows of the thrombectomy stent are the first grid cell rows, and the even-numbered rows are the second grid cell rows; or the even-numbered rows are the first grid cell rows, and the odd-numbered rows are the second grid cell rows; and in a direction perpendicular to the axial direction of the thrombectomy stent, the first grid cells are aligned with the gaps between every two adjacent second grid cells, and the second grid cells are aligned with the gaps between every two adjacent first grid cells. Such an arrangement is advantageous for uniform distribution of grid wires on respective segments of the thrombectomy stent and on the circumference of the cross section thereof, so that uniform support force can be provided and the thrombectomy effect is better.

Further, the width of grid wires of the grid cells is 0.05 mm to 0.16 mm; and the size of junctions between the grid cells is 0.25 mm to 0.45 mm. Preferably, the width of the grid wires of the grid cells is 0.07 mm to 0.14 mm.

Further, the thrombectomy stent has a first state and a second state; and in the second state, the shape of the grid cells changes. For example, after the change, the outer diameter of the middle segment of the thrombectomy stent is less than the outer diameters of the two ends thereof.

Further, in the first state, the shape of the grid cells is stable.

Further, in the first state, the size of the grid cells is 3 mm to 5 mm. Preferably, the size of the grid cells is 3.6 mm to 4.5 mm. The support force of the thrombectomy stent against the operation site is determined by the width and thickness of the grid wires of the grid cells, the size and arrangement of the grid cells and the roll-shaped open-ring structure of the thrombectomy stent together, where the roll-shaped open-ring structure can facilitate the adjustment of the support force. In the present invention, the thickness of the grid wires of the grid cells is as shown in the prior art. The thrombectomy stent is designed to have different outer diameters and lengths to adapt to cerebral vessels of different diameters and thrombi of different lengths.

Further, developing elements are disposed at the distal end of the thrombectomy stent. The developing elements are used for positioning the thrombectomy stent in the blood vessel during surgery. Preferably, the number of the developing elements at the ends of the grid cells at the distal end of the thrombectomy stent is 2-8. Preferably, the number is 4.

Further, the material of the thrombectomy stent includes a memory alloy. Further, the material of the thrombectomy stent includes a nickel-titanium alloy and/or a cobalt-based alloy.

Further, the thrombectomy device further comprises a push rod; and the proximal end of the thrombectomy stent is connected to a distal end of the push rod, and a developing element is disposed at the junction. Further, the developing element uses noble metal developing points and has strong developing performance, which can help a surgeon determine the position of the thrombectomy stent during surgery.

In one specific embodiment, the developing element at the junction of the proximal end of the thrombectomy stent and the distal end of the push rod is a developing ring; and the developing ring is sheathed at the junction.

In another specific embodiment, the proximal end of the thrombectomy stent is connected to the distal end of push rod by means of soldering, sleeve connection, linking or adhesive fixed connection. Preferably, the soldering includes silver soldering and/or gold soldering.

In still another specific embodiment, the proximal end of the thrombectomy stent is connected to the distal end of the push rod by means of soldering, sleeve connection or linking first and then adhesive fixed connection.

Further, the adhesive includes a UV adhesive and/or an epoxy resin adhesive.

Further, the material of the push rod includes a nickel-titanium alloy. Therefore, the push rod has good flexibility and resilience, which is convenient for pushing the thrombectomy device in the tortuous blood vessel.

Further, the distal end of the push rod is configured in a tapered step shape to provide a smooth transition when connected to the proximal end of the thrombectomy stent.

Further, the outer surface of the push rod is coated with a polymer material with a low friction coefficient. It facilitates reducing the friction of the push rod to provide a high push performance. The polymer material with a low friction coefficient includes polytetrafluoroethylene (PTFE) and/or polyethylene terephthalate (PET) plastic.

Further, the thrombectomy device further comprises an introducing sheath; and the introducing sheath is a double-layer tube, the material of the inner-layer tube including PTFE or/and high density polyethylene (HDPE), and the material of the outer-layer tube including nylon and/or Pebax. Pebax is a nylon elastomer. The introducing sheath serves to introduce the thrombectomy stent into a microcatheter along with the push rod. The microcatheter is a surgical accessory.

Further, an inner wall of a distal end of the inner-layer tube is configured to have smooth rounded transition.

Further, a handle is disposed at a proximal end of the introducing sheath.

The inventors further provide a thrombectomy device system, comprising a thrombectomy stent, a push rod and a catching member, wherein a proximal end of the thrombectomy stent is connected to the push rod, and the push rod is connected to the catching member; and the catching member is configured to receive the thrombectomy stent. In the present invention, the distal end refers to the end far away from an operator (such as a surgeon); and the proximal end refers to the end close to the operator (such as the surgeon).

Further, the catching member comprises a first end and a second end; the first end is connected to the proximal end of the thrombectomy stent or the push rod; the second end is provided with an opening; and the opening is configured for the thrombectomy stent and the push rod to pass through.

Preferably, the first end is fixedly connected to the proximal end of the thrombectomy stent or the push rod by means of sheathing outside.

Further, the catching member has a first state and a second state; in the first state, the thrombectomy stent is located outside the catching member; and in the second state, the thrombectomy stent is disposed inside the catching member.

Further, the transition from the first state to the second state is set as follows: the first end, extending out of a distal end of the microcatheter, and the thrombectomy stent are withdrawn into the microcatheter by means of the push rod pushing back the thrombectomy stent, and pass through the second end in the microcatheter, so that the first end is located at a proximal end of the catching member, and the second end is located at a distal end of the catching member, so that the thrombectomy stent is sheathed in the catching member. The microcatheter is a surgical accessory that is used for the surgical operation of the thrombectomy device system.

During the thrombectomy stent and the first end being pulled back into the microcatheter by the push rod, under action of the resistance or/and the friction of the microcatheter to the catching member, the withdrawing speed of the second end is less than the withdrawing speed of the first end, so that the thrombectomy stent and the first end can pass through the second end. The second end of the catching member is collapsed within the microcatheter, the outer surface of the catching member is in contact with the inner surface of the microcatheter, and the microcatheter limits natural stretching of the catching member. When the thrombectomy stent and the first end of the catching member, which extend out of the microcatheter, are pulled back by the push rod, the resistance or/and the friction of the microcatheter to the catching member hinders the withdrawal of the second end of the catching member, so that the thrombectomy stent and the first end can pass through the second end such that the thrombectomy stent can be received in the catching member.

Preferably, in the first state, the first end is located at the distal end of the catching member, and the second end is located at the proximal end of the catching member; and the transition from the first state to the second state enables the catching member to turn inside out and shift front and back.

Further, in the second state, the opening of the second end tends to close. The tendency to close is beneficial to preventing the thrombus on the thrombectomy stent received inside from being detached from the opening of the second end. Preferably, the catching member is woven in such a manner that the opening of the second end thereof tends to open in the first state; and when in the second state, i.e., after the catching member turns inside out, the opening in the second end tends to close again. The tendency to open in the first state is beneficial to generating greater friction with the microcatheter, so that when the first state is changed to the second state, the thrombectomy stent and the first end easily pass through the second end such that the thrombectomy stent is received by the catching member.

Further, the catching member is of a flexible structure.

Further, the catching member is made of metal and/or a polymer material. Preferably, the catching member is woven with metal wires or polymer material wires. Preferably, the metal wires are made of a memory alloy such as a nickel-titanium alloy.

Preferably, the catching member is in the shape of a stocking and is self-expanding.

Further, the length of the catching member is greater than that of the thrombectomy stent.

Further, in the second state, the thrombectomy stent wrapped by the catching member and the catching member are further pulled into the catheter. The catheter is a surgical accessory that is used for a surgical operation of the thrombectomy device system and serves to guide the microcatheter and the thrombectomy stent within the microcatheter into a corresponding site in the blood vessel.

Further, the thrombectomy stent comprises a plurality of identical or different grid cells; and the catching member is of a mesh structure, the grid size of which is less than that of the grid cells.

Further, the grid cells are connected to each other in a mesh shape.

Further, the shape of the grid cells includes one or more of a pattern composed of arcs and a pattern composed of polygons, arcs and straight lines.

Further, the shape of the grid cells includes one or more of a circle, an ellipse, a quadrangle, a triangle, a diamond and a trapezoid.

Further, the shape of the grid cells includes a pattern composed of a plurality of arcs.

Further, the plurality of grid cells are sequentially arranged in rows, and the grid cells of two adjacent rows are arranged in a staggered manner. Preferably, the rows are parallel to the axial direction of the thrombectomy stent. That is, in a direction perpendicular to the axial direction of the thrombectomy stent, the grid cells of one of two adjacent rows align to gaps of every two adjacent grid cells of the other row. With such a design, the thrombectomy stent is more collapsible and more adaptable to small blood vessels and is easier to be collected into the introducing sheath.

Further, the grid cell is enclosed by four of the grid cells adjacent to each other.

Preferably, the grid cells include first grid cells and second grid cells; the first grid cell is enclosed by four of the second grid cells adjacent to each other; and the second grid cell is enclosed by four of the first grid cells adjacent to each other.

Further, the grid cells include first grid cells and second grid cells; a plurality of first grid cells are sequentially arranged in first grid cell rows which are parallel to the axial direction of the thrombectomy stent; a plurality of second grid cells are sequentially arranged in second grid cell rows which are parallel to the axial direction of the thrombectomy stent; and the first grid cell rows and the second grid cell rows are alternately arranged in the axial direction of the thrombectomy stent and arranged in a staggered manner in a direction perpendicular to the axial direction of the thrombectomy stent. The arrangement is as follows: the odd-numbered rows of the thrombectomy stent are the first grid cell rows, and the even-numbered rows are the second grid cell rows; or the even-numbered rows are the first grid cell rows, and the odd-numbered rows are the second grid cell rows; and in a direction perpendicular to the axial direction of the thrombectomy stent, the first grid cells are aligned with the gaps between every two adjacent second grid cells, and the second grid cells are aligned with the gaps between every two adjacent first grid cells. Such an arrangement is advantageous for uniform distribution of grid wires on respective segments of the thrombectomy stent and on the circumference of the cross section thereof, so that uniform support force can be provided and the thrombectomy effect is better.

Further, the meshes in the middle are larger than the meshes on both sides and are stronger in support force, so that the thrombectomy stent can be better embedded into the thrombus.

Preferably, the width of grid wires of the grid cells is 0.05 mm to 0.16 mm; and the size of junctions between the grid cells is 0.25 mm to 0.45 mm. Preferably, the width of the grid wires of the grid cells is 0.07 mm to 0.14 mm.

Further, the thrombectomy stent has an expanded state and a contracted state; the expanded state includes a third state and a fourth state; and in the fourth state, the grid cells change in shape under an external force. For example, after the change, the outer diameter of the middle segment of the thrombectomy stent is less than the outer diameters of the two ends thereof. The expanded state refers to a state in which the thrombectomy stent is released into the blood vessel and is not sheathed with the microcatheter and/or the introducing sheath; and the contracted state refers to a state in which the thrombectomy stent is withdrawn into the microcatheter and/or the introducing sheath.

Further, in the third state, the shape of the grid cells is stable.

Further, in the third state, the size of the grid cells is 3 mm to 5 mm. Preferably, the size of the grid cells is 3.6 mm to 4.5 mm. The support force of the thrombectomy stent against the operation site is determined by the width and thickness of the grid wires of the grid cells, the size of the grid cells and the roll-shaped open-ring structure of the thrombectomy stent together, where the roll-shaped open-ring structure can facilitate the adjustment of the support force. In the present invention, the thickness of the grid wires of the grid cells is as shown in the prior art. The thrombectomy stent is designed to have different outer diameters and lengths to adapt to cerebral vessels of different diameters and thrombi of different lengths.

Further, the thrombectomy stent is roll-shaped; and the cross section of the thrombectomy stent is of an open-ring structure. The outer diameter of the thrombectomy stent varies with the degree of curling of the thrombectomy stent. The open-ring roll-shaped design facilitates the adjustment of curling tightness as needed so as to adjust the outer diameter of the thrombectomy stent to adapt to the size of different blood vessels and adapt to different support forces. When a blood vessel is small, the degree of curling is increased, and the outer diameter is reduced; and vice versa. A suitable support force is beneficial to improving the fusion of the thrombectomy stent and a thrombus without damaging the blood vessel and to increasing the capability of catching the thrombus. The support force here refers to a tension of the thrombectomy stent against an inner wall of the blood vessel at the operation site.

Further, developing elements are disposed on the thrombectomy stent. The shape of the developing elements may be set as needed, and may be, for example, line-shaped, ring-shaped, mesh-shaped and/or dot-shaped. The developing elements are used for positioning the thrombectomy stent in the blood vessel during surgery.

Further, the developing element uses noble metal developing points and has strong developing performance.

Preferably, the number of the developing elements is greater than or equal to 2, and the developing elements are uniformly distributed around the roll-shaped circumference of the thrombectomy stent.

Preferably, the number of the developing elements is greater than or equal to 3.

Further, the developing elements are disposed at both a distal end and a proximal end of the thrombectomy stent.

Further, the number of the developing elements at the distal end of the thrombectomy stent is greater than or equal to 2, and the developing elements at the distal end of the thrombectomy stent are uniformly distributed at the distal end of the thrombectomy stent; and the number of the developing elements at the proximal end of the thrombectomy stent is greater than or equal to 2, and the developing elements at the proximal end of the thrombectomy stent are uniformly distributed at the proximal end of the thrombectomy stent.

Preferably, the number of the developing elements at the distal end of the thrombectomy stent is greater than or equal to 2, and the developing elements at the distal end of the thrombectomy stent are uniformly distributed at the distal end of the thrombectomy stent around the roll-shaped circumference of the thrombectomy stent; and the number of the developing elements at the proximal end of the thrombectomy stent is greater than or equal to 2, and the developing elements at the proximal end of the thrombectomy stent are uniformly distributed at the proximal end of the thrombectomy stent around the roll-shaped circumference of the thrombectomy stent.

Preferably, developing elements are disposed at a middle segment of the thrombectomy stent. In the present invention, the middle segment of the thrombectomy stent refers to a segment between the distal end and the proximal end of the thrombectomy stent.

Further, the number of the developing elements at the distal end of the thrombectomy stent is greater than or equal to 2, and the developing elements at the distal end of the thrombectomy stent are uniformly distributed at the distal end of the thrombectomy stent; and the number of the developing elements at the proximal end of the thrombectomy stent is greater than or equal to 2, and the developing elements at the proximal end of the thrombectomy stent are uniformly distributed at the proximal end of the thrombectomy stent; and the number of the developing elements at the middle segment of the thrombectomy stent is greater than or equal to 2, and the developing elements at the middle segment of the thrombectomy stent are uniformly distributed at the middle segment of the thrombectomy stent.

Preferably, the number of the developing elements at the distal end of the thrombectomy stent is greater than or equal to 2, and the developing elements at the distal end of the thrombectomy stent are uniformly distributed at the distal end of the thrombectomy stent around the roll-shaped circumference of the thrombectomy stent; and the number of the developing elements at the proximal end of the thrombectomy stent is greater than or equal to 2, and the developing elements at the proximal end of the thrombectomy stent are uniformly distributed at the proximal end of the thrombectomy stent around the roll-shaped circumference of the thrombectomy stent; and the number of the developing elements at the middle segment of the thrombectomy stent is greater than or equal to 2, and the developing elements at the middle segment of the thrombectomy stent are uniformly distributed at the middle segment of the thrombectomy stent around the roll-shaped circumference of the thrombectomy stent.

Further, the developing elements include developing lines.

Further, one end of the developing line is disposed at the distal end or a distal end face of the thrombectomy stent, and the other end thereof is disposed at the proximal end or a proximal end face of the thrombectomy stent.

Further, the number of the developing lines is greater than or equal to 3, and the developing lines are uniformly arranged on the thrombectomy stent.

Preferably, the thrombectomy stent is roll-shaped; the cross section of the thrombectomy stent is of an open-ring structure; and the number of the developing lines is greater than or equal to 3, and the developing lines extend in the axial direction of the thrombectomy stent and are uniformly arranged on the thrombectomy stent around the roll-shaped circumference of the thrombectomy stent.

Further, the developing lines extend in the direction of the roll-shaped circumference of the thrombectomy stent.

Further, the developing lines not only axially extend along the thrombectomy stent but also extend back and forth in the direction of the roll-shaped circumference of the thrombectomy stent.

Preferably, the number of the developing lines is greater than or equal to 3, and the developing lines are uniformly arranged on the thrombectomy stent around the roll-shaped circumference of the thrombectomy stent.

Further, the developing elements are disposed in a manner including one or more of spraying or brushing a developing material to the thrombectomy stent or mounting the developing elements onto the thrombectomy stent by means of winding, buckling, perforating, soldering or bonding.

Further, the entire thrombectomy stent is covered with a developing material.

Further, the developing elements include a developing mesh; the developing mesh is located at the most distal end of the thrombectomy stent to close an opening at the distal end of the thrombectomy stent.

Further, the thrombectomy stent comprises a plurality of identical or different grid cells; and the grid size of the developing mesh is less than that of the grid cells. Therefore, during thrombectomy, it can not only display the position of the distal end of the thrombectomy stent but also catch the detached thrombus during thrombectomy.

Further, the distal end of the thrombectomy stent is in an open state. During thrombectomy, the middle segment of the thrombectomy stent is often fused with a thrombus, and at this time the middle segment of the thrombectomy stent is often deformed so that the outer diameter of the segment is reduced. If the distal end of the thrombectomy stent is in a closed state, both the outer diameters of the middle segment and the distal end of the thrombectomy stent are reduced during thrombectomy, so that the thrombus is easy to be detached from the thrombectomy stent during thrombectomy due to the resistance of the vascular wall. If the distal end of the thrombectomy stent is in the open state, the outer diameter of the middle segment (the thrombectomy part) of the thrombectomy stent is reduced, and the outer diameters of two ends of the thrombectomy stent are greater than that of the middle segment, and at this time the thrombectomy stent is dumbbell-shaped, and especially the outer diameter of the distal end of the thrombectomy stent is greater than that of the middle segment of the thrombectomy stent, so that the thrombus is not easy to be detached from the stent during thrombectomy. Therefore, the thrombectomy stent in the state of being open at the distal end is obviously better, in thrombus fusion and catching ability, i.e., in thrombectomy effect, than the thrombectomy stent in the state of being closed at the distal end.

Further, the proximal end of the thrombectomy stent is in an open state. The outer diameter of the proximal end is greater than that of the middle segment of the thrombectomy stent during thrombectomy, so that the thrombus is not easy to be detached from the proximal end.

Preferably, the closer to the most distal end of the thrombectomy stent is, the smaller the perimeter of the cross section of the distal end of the thrombectomy stent. It facilitates the distal end of the thrombectomy stent to be curled to be smaller so as to extend into a smaller blood vessel, which expands the range of application of the thrombectomy stent.

Preferably, the closer to the most proximal end of the thrombectomy stent is, the smaller the perimeter of the cross section of the proximal end of the thrombectomy stent. It facilitates the thrombectomy stent to be better collapsed into the introducing sheath and the microcatheter.

Preferably, the cross section of the most proximal end of the thrombectomy stent is reduced to a dot.

Preferably, the cross section of the distal end of the thrombectomy stent is C-shaped.

Preferably, the cross section of the proximal end of the thrombectomy stent is C-shaped.

Further, the material of the thrombectomy stent includes a memory alloy. Preferably, the material of the thrombectomy stent includes a nickel-titanium alloy and/or a cobalt-based alloy.

Further, the proximal end of the thrombectomy stent is connected to a distal end of the push rod, and a developing element is disposed at the junction.

Further, the developing element at the junction of the proximal end of the thrombectomy stent and the distal end of the push rod is a developing ring; and the developing ring is sheathed at the junction.

Further, the proximal end of the thrombectomy stent is connected to the distal end of the push rod by means of soldering, sleeve connection, linking or adhesive fixed connection.

Preferably, the proximal end of the thrombectomy stent is connected to the distal end of the push rod by means of soldering, sleeve connection or linking first and then adhesive fixed connection.

Further, the adhesive includes a UV adhesive and/or an epoxy resin adhesive.

Further, the material of the push rod includes a nickel-titanium alloy. Therefore, the push rod has good flexibility and resilience, which is convenient for pushing the thrombectomy device in the tortuous blood vessel.

Further, the distal end of the push rod is configured in a tapered shape to provide a smooth transition when connected to the proximal end of the thrombectomy stent.

Further, the outer surface of the push rod is coated with a polymer material with a low friction coefficient. It facilitates reducing the friction of the push rod to provide a high push performance. The polymer material with a low friction coefficient includes polytetrafluoroethylene (PTFE) and/or polyethylene terephthalate (PET) plastic.

Further, an introducing sheath is further comprised, wherein the introducing sheath is a double-layer tube, the material of the inner-layer tube including PTFE and/or HDPE, and the material of the outer-layer tube including nylon and/or other polymer material (such as Pebax). The introducing sheath serves to introduce the thrombectomy stent into a microcatheter along with the push rod.

Further, an inner wall of a distal end of the inner-layer tube is configured to have smooth rounded transition.

Further, a handle is disposed at a proximal end of the introducing sheath.

The beneficial effects are as follows:

1. The catching member can effectively catch a thrombus detached during the thrombectomy. By means of the transition between the first state and the second state of the catching member, the thrombectomy stent can be simply, conveniently and repeatedly released from or sheathed to the catching member.

2. After the thrombectomy stent is completely mounted into the catching member, the opening of the catching member is closed, which is more advantageous for preventing the thrombus from being detached from the thrombectomy stent. Particularly, the catching member has a mesh structure of small meshes or a mesh-free bag structure.

3. The number of developing elements is increased on the effective length of the thrombectomy stent (i.e., from the proximal end to the distal end of the thrombectomy stent), so that the surgeon can accurately determine the position of the thrombectomy stent during surgery.

4. Additionally providing developing lines in the number of greater than or equal to 3 on the thrombectomy stent can accurately display the expansion state and specific position of the thrombectomy stent during thrombectomy so as to judge the fusion of the thrombectomy stent and the blood vessel, which facilitates the surgeon's judgment and the surgical operation and reduces the surgical time.

5. The entire thrombectomy stent is sprayed with a developing material such as gold or platinum, so that the entire thrombectomy stent can be developed so as to accurately display the expansion state and specific position of the thrombectomy stent during thrombectomy, which facilitates the surgeon's judgment and the surgical operation and reduces the surgical time.

6. Additionally providing a developing mesh at the distal end of the thrombectomy stent can not only display the position of the thrombectomy stent but also catch the thrombus detached during thrombectomy, especially when the grid size of the developing mesh is less than the grid size of the grid cells of the thrombectomy stent.

7. The special incision design of the thrombectomy stent ensures the flexibility of the thrombectomy stent and good thrombus catching ability.

8. With the special incision design of the thrombectomy stent, the thrombus can be effectively attached and prevented from being detached from the thrombectomy stent during thrombectomy.

9. The thrombectomy stent and the push rod have good flexibility and resilience and can freely pass through the microcatheter and the tortuous blood vessel.

10. When the grid cells of the thrombectomy stent are of a pattern enclosed by arcs, the side wall of the thrombectomy stent is certainly rounded, thereby reducing the probability of damage to the blood vessel during the surgery.

11. The thrombectomy stent is designed to have an open-ring structure, so that the thrombectomy stent has good flexibility and can pass through the tortuous blood vessel and reach the treatment site smoothly.

DETAILED DESCRIPTION OF EMBODIMENTS

The present invention will be further described with reference to the accompanying drawings and specific embodiments, and the scope of the present invention is not limited to the following embodiments. Variations and advantages that may be conceived by those skilled in the art are included within the present invention without departing from the spirit and scope of the present invention, and the scope of protection shall be defined in the appended claims.

Embodiment 1

Figure 1:
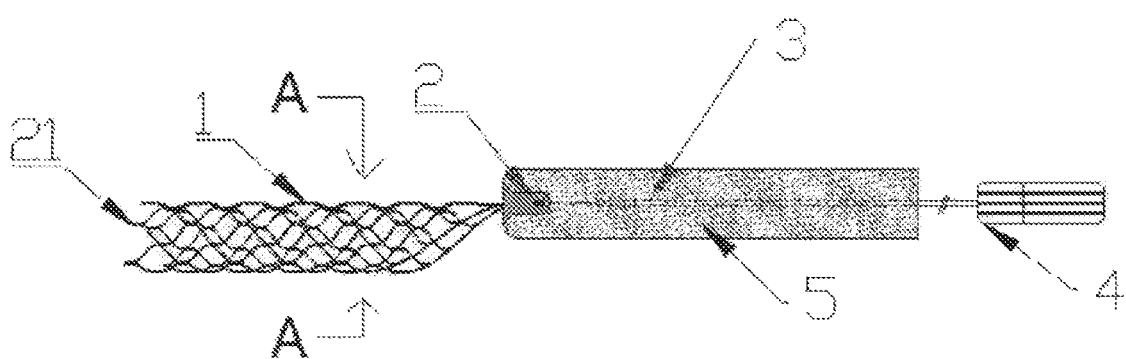
FIG. 1 is a structural schematic diagram of a thrombectomy device system according to the present invention.

FIG. 1 shows one specific embodiment of a thrombectomy device system according to the present invention. In this embodiment, the thrombectomy device system comprises a thrombectomy stent 1, a developing ring 2, a push rod 3, an introducing sheath 4 and a catching member 5. A proximal end of the thrombectomy stent 1 is connected to a distal end of the push rod 3, and the developing ring 2 (which is the first type of developing elements 21) is disposed at the junction. The push rod 3 is connected to the introducing sheath 4. Developing elements 21 are disposed at a distal end of the thrombectomy stent 1. Both the distal end and the proximal end of the thrombectomy stent 1 are in an open state. The proximal end of the thrombectomy stent 1 is also connected to the catching member 5.

Figure 4A:
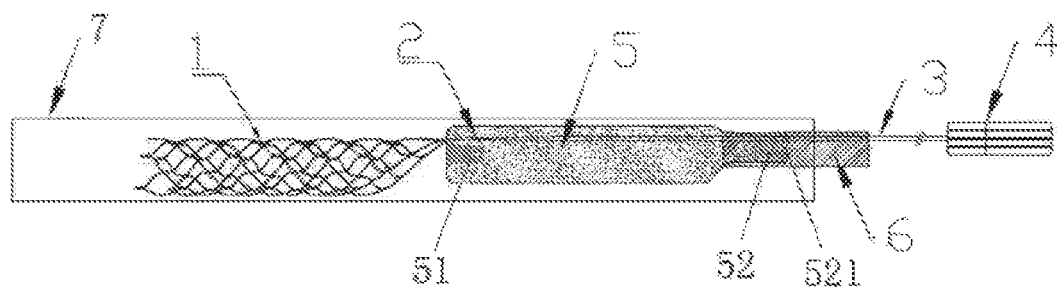
FIG. 4A is a structural schematic diagram of the thrombectomy device system in a first state.
Figure 4B:
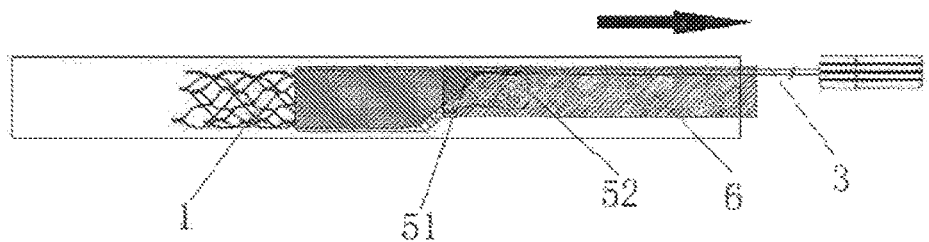
FIG. 4B is a structural schematic diagram of the thrombectomy device system during the transition from the first state to a second state.

The catching member 5 has a first state and a second state. FIG. 4A shows the case in the first state, in which the catching member 5 is sheathed outside the push rod 3, and the end connected to the thrombectomy stent 1 is a first end 51 of the catching member 5 and is located at a distal end of the catching member 5; and the other end is a second end 52 of the catching member 5 and is located at a proximal end of the catching member 5. FIG. 4B shows transition of the catching member 5 from the first state to the second state; and FIG. 4C shows the case in the second state.

Figure 4C:
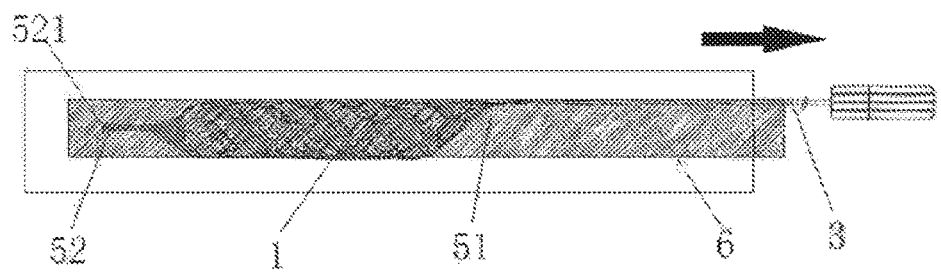
FIG. 4C is a structural schematic diagram of the thrombectomy device system in the second state.

FIGS. 4A, 4B and 4C are combined to learn the transition from the first state to the second state more intuitively as follows. First, the state transition is to sheath the thrombectomy stent 1 after the thrombectomy into the catching member 5 so as to prevent detachment of the thrombus. Specifically, after completing the thrombectomy, the thrombectomy stent 1 needs to be collapsed into a microcatheter 6 and withdrawn from a blood vessel 7 together with the microcatheter 6. The thrombectomy stent 1 has an expanded state and a contracted state. The expanded state refers to a state in which the thrombectomy stent is released into the blood vessel and is not sheathed with the microcatheter and/or the introducing sheath; and the contracted state refers to a state in which the thrombectomy stent is withdrawn into the microcatheter and/or the introducing sheath. The expanded state further includes a third state and a fourth state. In the fourth state, grid cells of the thrombectomy stent 1 change in shape under an external force, for example, during the thrombectomy, a middle segment of the thrombectomy stent is inserted into the thrombus such that its outer diameter is reduced so as to form a shape narrow in the middle and wide at both ends. In the third state, the thrombectomy stent 1 is naturally stretched and has a stable shape.

In the first state, the second end 52 is located inside the microcatheter 6, and the push rod 3 passes through an opening 521 of the second end 52; and the thrombectomy stent 1 and the first end 51 are located outside the microcatheter 6. The thrombectomy stent 1 is in the expanded state. The thrombectomy stent 1 and the first end 51 are pulled back into the microcatheter 6 by the push rod 3. At the same time, due to the friction between the second end 52 and the inner wall of the microcatheter 6, the second end 52 remains stationary or has a withdrawing speed less than that of the first end 51 and the thrombectomy stent 1, so that the first end 51 and the thrombectomy stent 1 pass through the second end 52. The first end 51 changes from the distal end of the catching member 5 to the proximal end of the catching member 5, while the second end 52 changes from the proximal end of the catching member 5 to the distal end of the catching member 5. At this time, the catching member 5 turns inside out and shifts front and back, so that the thrombectomy stent 1 is sheathed in the catching member 5, thereby realizing the transition from the first state to the second state.

In one specific embodiment, the catching member 5 is a catching mesh woven with memory alloy wires in such a manner that in the first state, the opening 521 of the second end 52 tends to open so as to be in closer contact with the microcatheter 6, so that greater friction will be produced when the two move relative to each other; and in the second state, the catching member 5 turns inside out, and the opening 521 of the second end 52 tends to close (as shown in FIG. 4C), so that the thrombus on the thrombectomy stent 1 received by the catching member 5 is less likely to detach.

When the thrombectomy is performed again, the catching mesh 5 needs to be turned over in vitro and is then introduced into the body through the microcatheter 6.

It is turned over in such a manner that an operator (such as a surgeon) holds the catching mesh 5 and pushes the push rod 3 forward till the catching mesh 5 is completely turned over, thus completing the transition from the second state to the first state.

The catching member 5 is made of metal and/or a polymer material. The catching member 5 may be a catching mesh of a mesh structure or may be a mesh-free bag structure. The mesh structure can facilitate the flow of blood without clogging the blood. When the catching member is a catching mesh, its mesh size is less than the grid size of the grid cells of the thrombectomy stent, or the meshes of the catching mesh are small enough to prevent detachment of most thrombi.

Figure 2:
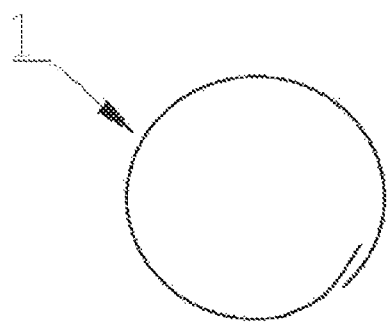
FIG. 2 is a structural schematic diagram of a section A-A in FIG. 1.
Figure 3:
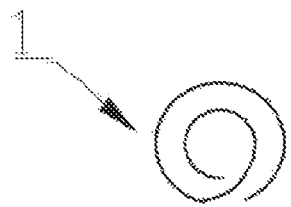
FIG. 3 is a structural schematic diagram of a thrombectomy stent in FIG. 2 in another state.

The section A-A of FIG. 1 is as shown in FIG. 2, and it can be seen that the cross section of the thrombectomy stent 1 is an open ring. It can be seen in conjunction with FIG. 1 that the thrombectomy stent 1 is roll-shaped. The outer diameter of the thrombectomy stent 1 can be changed by adjusting the degree of curling of the thrombectomy stent 1, for example, after the degree of curling is increased, the outer diameter of the thrombectomy stent 1 is reduced, as shown in FIG. 3, and vice versa.

Embodiment 2

Figure 5:
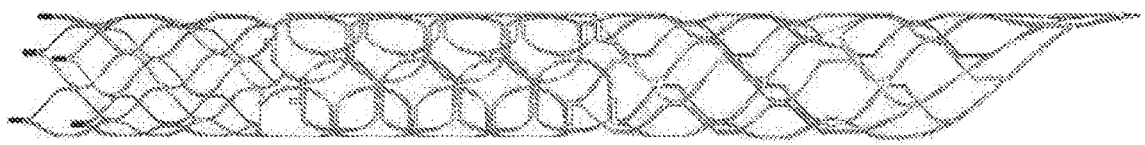
FIG. 5 is a preferred structural schematic diagram of the thrombectomy stent according to the present invention.

In this embodiment, as shown in FIG. 5, the meshes in the middle of the thrombectomy stent are greater than the meshes on both sides, and the meshes in the middle are stronger in support force, so that the thrombectomy stent can be better embedded into the thrombus by means of the meshes in the middle, and at the same time a better incising effect is achieved when the thrombus is incised.

Embodiment 3

Figure 6:
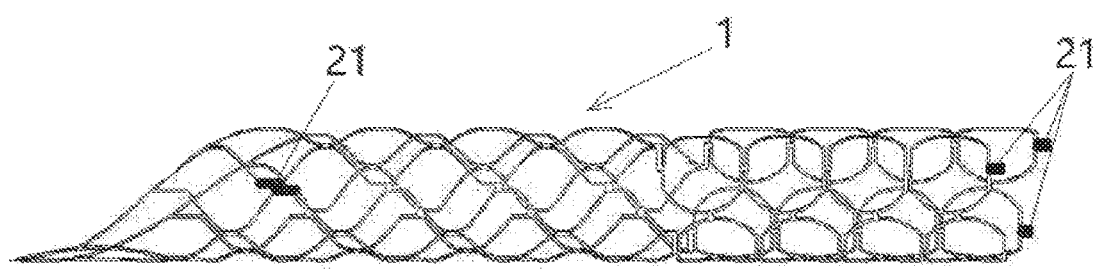
FIGS. 6-11 are structural schematic diagrams of several specific embodiments about the design and distribution of developing elements.

In this embodiment, developing elements 21 are disposed at both the distal end and the proximal end of the thrombectomy stent 1, as shown in FIG. 6. Three developing elements 21 are located at the distal end and are uniformly distributed on the circumference of the roll-shaped structure of the thrombectomy stent 1. In the present invention, uniform distribution on the circumference of the roll-shaped structure of the thrombectomy stent 1 means that the distance therebetween on the circumference is the same or similar. One or more developing elements 21 are located at the proximal end, and in the case of a plurality of developing elements, the developing elements are uniformly distributed on the circumference of the roll-shaped structure of the thrombectomy stent 1. The number of the developing elements 21 at the distal end and the proximal end is not limited to that shown in FIG. 6 and may be one or more.

Embodiment 4

Figure 7:
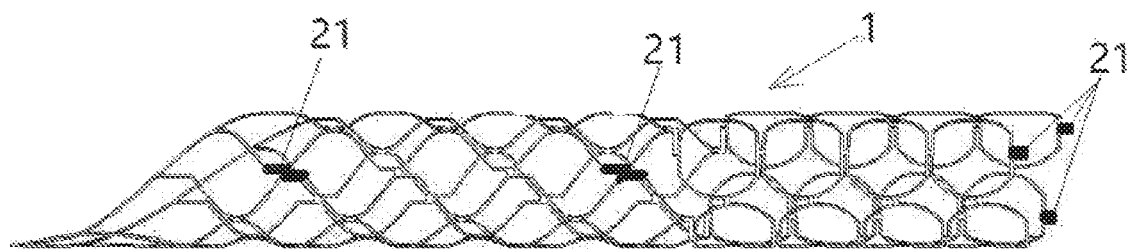

In this embodiment, developing elements 21 are disposed at the distal end, the middle segment and the proximal end of the thrombectomy stent 1, as shown in FIG. 7. Three developing elements 21 are located at the distal end and are uniformly distributed on the circumference of the roll-shaped structure of the thrombectomy stent 1. One or more developing elements 21 are located at the middle segment, and in the case of a plurality of developing elements, the developing elements are uniformly distributed on the circumference of the roll-shaped structure of the thrombectomy stent 1. One or more developing elements 21 are located at the proximal end, and in the case of a plurality of developing elements, the developing elements are uniformly distributed on the circumference of the roll-shaped structure of the thrombectomy stent 1. The number of the developing elements 21 at the distal end, the middle segment and the proximal end is not limited to that shown in FIG. 6 and may be one or more.

Embodiment 5

Figure 8:
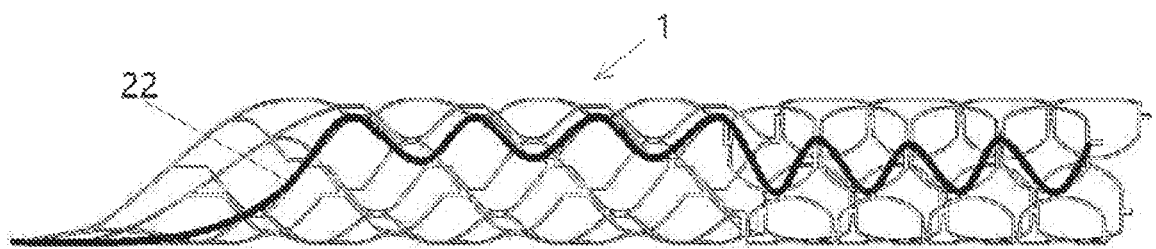

In this embodiment, the developing elements include developing lines 22. One end of the developing line 22 is disposed at the distal end of the thrombectomy stent 1, and the other end thereof is disposed on the proximal end face of the thrombectomy stent 1, as shown in FIG. 8. The developing line 22 extends back and forth in a wave shape in the direction of the roll-shaped circumference of the thrombectomy stent 1 while extending in the axial direction of the thrombectomy stent 1. The number of the developing lines 22 may be one or more. In the case of a plurality of developing lines, the developing lines are uniformly distributed on the circumference of the roll-shaped structure of the thrombectomy stent 1.

Embodiment 6

Figure 9:
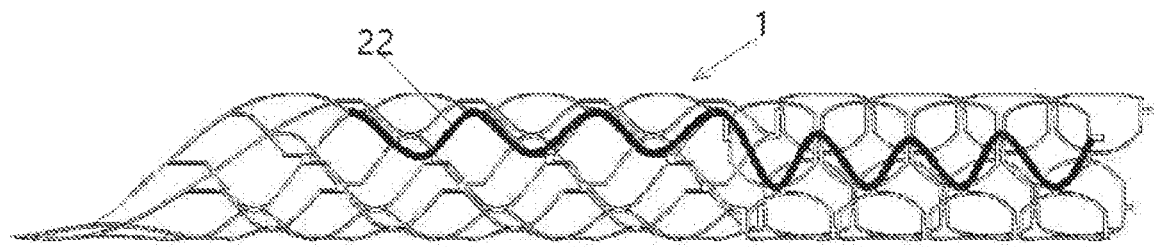

In this embodiment, the developing elements include developing lines 22. One end of the developing line 22 is disposed at the distal end of the thrombectomy stent 1, and the other end thereof is disposed at the proximal end of the thrombectomy stent 1, but does not reach the proximal end face, as shown in FIG. 9. The developing line 22 extends back and forth in a wave shape in the direction of the roll-shaped circumference of the thrombectomy stent 1 while extending in the axial direction of the thrombectomy stent 1. The number of the developing lines 22 may be one or more. In the case of a plurality of developing lines, the developing lines are uniformly distributed on the circumference of the roll-shaped structure of the thrombectomy stent 1.

Embodiment 7

In this embodiment, the developing elements include developing lines. One end of the developing line is disposed at the distal end of the thrombectomy stent, and the other end thereof is disposed at the proximal end of the thrombectomy stent. The developing lines are straight lines and extend in the axial direction of the thrombectomy stent. The number of the developing lines may be one or more. In the case of a plurality of developing lines, the developing lines are uniformly distributed on the circumference of the roll-shaped structure of the thrombectomy stent.

Embodiment 8

In this embodiment, the developing elements include developing lines. The developing lines extend in the direction of the roll-shaped circumference of the thrombectomy stent. A plurality of developing lines are provided. The developing lines are disposed at the distal end, the middle segment and the proximal end of the thrombectomy stent.

Embodiment 9

In this embodiment, the developing elements include developing lines. One developing line is provided. The developing line extends back and forth along the roll-shaped circumference of the thrombectomy stent while extending along the axis of the thrombectomy stent. One end of the developing line is disposed at the distal end of the thrombectomy stent, and the other end thereof is disposed at the proximal end of the thrombectomy stent.

Embodiment 10

Figure 10:
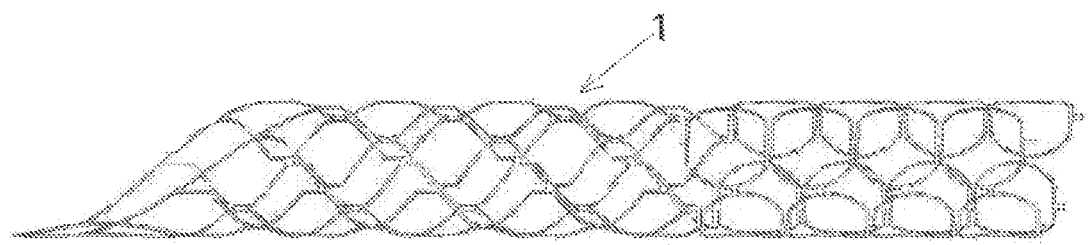

In this embodiment, the entire thrombectomy stent 1 is sprayed or brushed with a developing material, as shown in FIG. 10.

Embodiment 11

Figure 11:
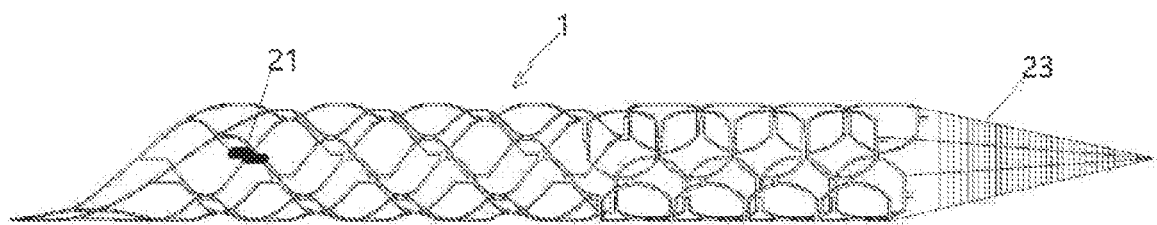

In this embodiment, developing elements 21 are disposed at the proximal end of the thrombectomy stent 1, and a developing mesh 23 is disposed at the distal end, as shown in FIG. 11. The developing mesh 23 is one type of the developing elements 21. The developing mesh 23 is located at the most distal end of the thrombectomy stent to close the opening at the distal end of the thrombectomy stent 1. The grid size of the developing mesh 23 is less than that of the grid cells of the thrombectomy stent 1. One or more developing elements 21 are located at the proximal end, and in the case of a plurality of developing elements, the developing elements are uniformly distributed on the circumference of the roll-shaped structure of the thrombectomy stent 1.

Embodiment 12

Figure 12:
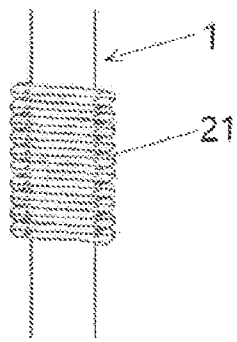
FIGS. 12-15 are structural schematic diagrams of several specific embodiments regarding the arrangement of developing elements.

In this embodiment, the developing elements 21 are disposed on the thrombectomy stent 1 by winding, as shown in FIG. 12. For example, the developing elements 21 at the proximal end of the thrombectomy stent 1 are wound on the thrombectomy stent 1.

Embodiment 13

Figure 13:
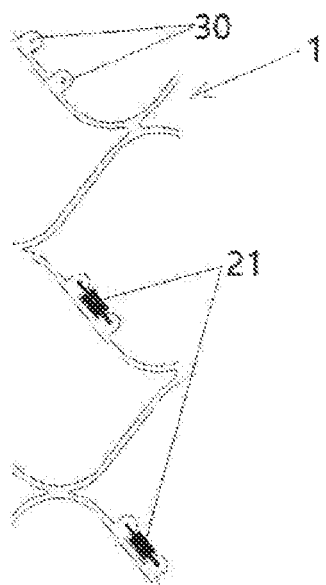
Figure 14:
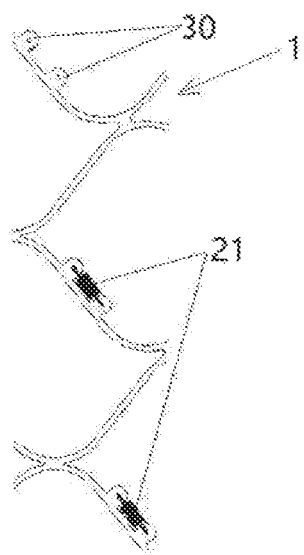

In this embodiment, attaching elements 30 are disposed on the thrombectomy stent 1, and the developing elements 21 are mounted on the attaching elements 30, as shown in FIGS. 13 and 14. The mounting may be achieved by perforating (as shown in FIG. 13) or buckling (as shown in FIG. 14). In this embodiment, the mounting may be for the developing elements 21 at any position, preferably for the developing elements 21 at the proximal end of the thrombectomy stent 1.

Embodiment 14

Figure 15:
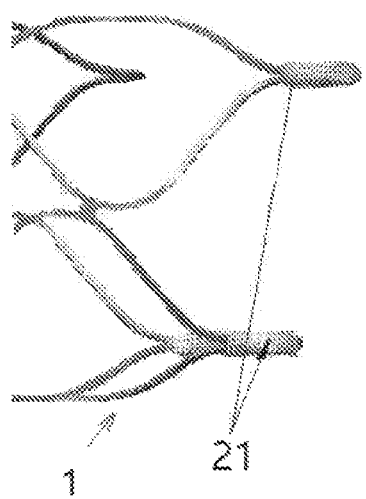

In this embodiment, the developing elements 21 are mounted to the thrombectomy stent 1 by winding, or the developing elements 21 are annularly sheathed on the thrombectomy stent 1, as shown in FIG. 15. In this embodiment, the mounting may be for the developing elements 21 at any position, preferably for the developing elements 21 at the distal end of the thrombectomy stent 1.

Embodiment 15

Figure 16:
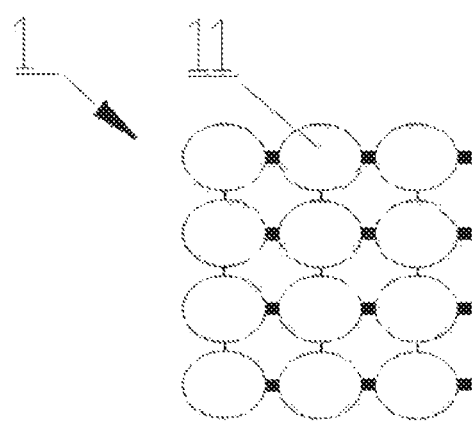
FIG. 16 is incision pattern I of the thrombectomy stent.

In this embodiment, the incision pattern of the thrombectomy stent is as shown in FIG. 16. The thrombectomy stent 1 comprises a plurality of identical grid cells 11 connected to each other. The grid cells 11 are elliptical.

Embodiment 16

Figure 17:
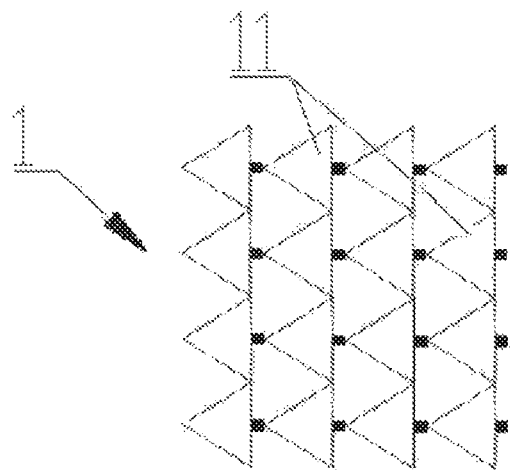
FIG. 17 is incision pattern II of the thrombectomy stent.

In this embodiment, the incision pattern of the thrombectomy stent is as shown in FIG. 17. The thrombectomy stent 1 comprises a plurality of grid cells 11 connected to each other. The grid cells 11 are triangular.

Embodiment 17

Figure 18:
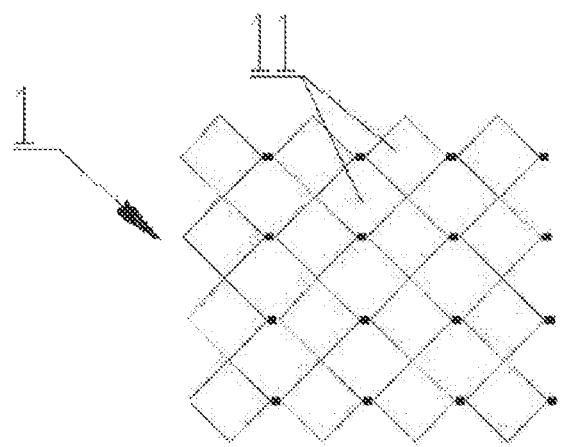
FIG. 18 is incision pattern III of the thrombectomy stent.

In this embodiment, the incision pattern of the thrombectomy stent is as shown in FIG. 18. The thrombectomy stent 1 comprises a plurality of grid cells 11 connected to each other. The grid cells 11 are quadrangular.

Embodiment 18

In this embodiment, the grid cells are elliptical.

Embodiment 18.1

Figure 19:
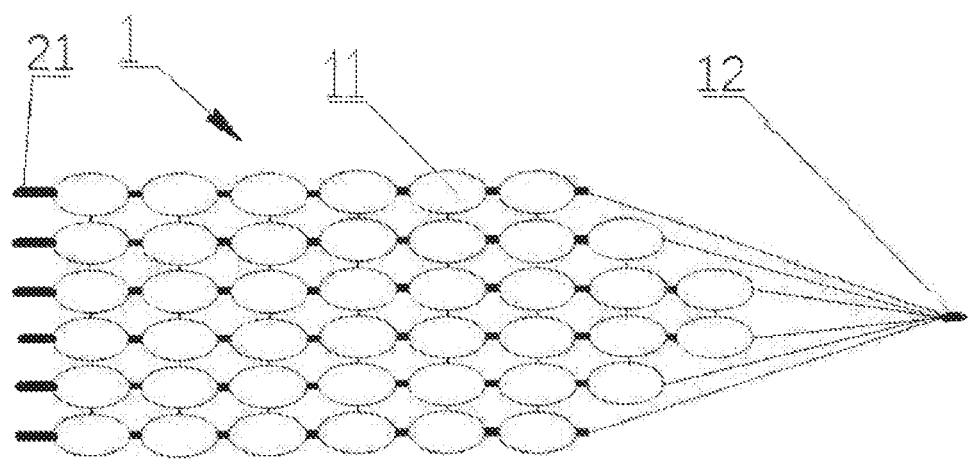
FIG. 19 is incision pattern IV of the thrombectomy stent.

In this embodiment, the incision pattern of the thrombectomy stent is as shown in FIG. 19. The thrombectomy stent 1 comprises a plurality of grid cells 11 connected to each other. The distal end of the thrombectomy stent 1 is provided with six developing elements 21 which extend along the distal end of the thrombectomy stent. The thrombectomy stent 1 is provided with one most proximal end 12.

Embodiment 18.2

Figure 20:
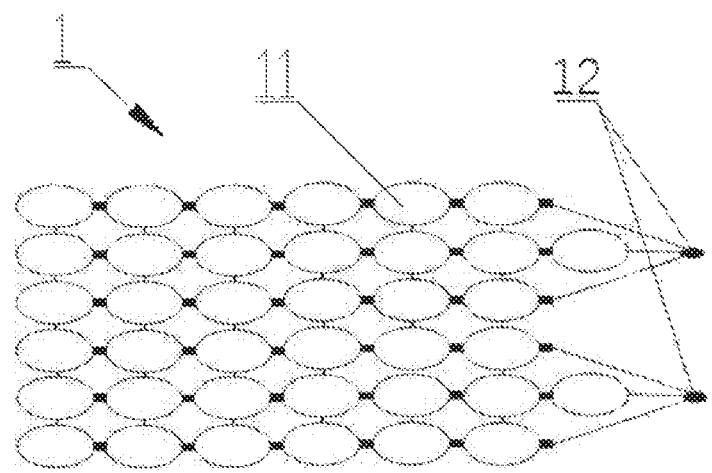
FIG. 20 is incision pattern V of the thrombectomy stent.

In this embodiment, the incision pattern of the thrombectomy stent is as shown in FIG. 20. The thrombectomy stent 1 comprises a plurality of grid cells 11 connected to each other. The thrombectomy stent 1 is provided with two proximal ends 12.

Embodiment 18.3

Figure 21:
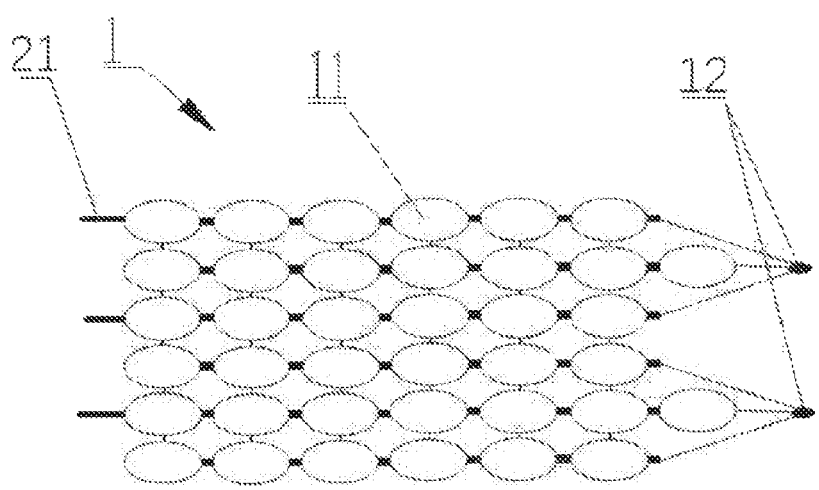
FIG. 21 is incision pattern VI of the thrombectomy stent.

In this embodiment, the incision pattern of the thrombectomy stent is as shown in FIG. 21. The thrombectomy stent 1 comprises a plurality of grid cells 11 connected to each other. The distal end of the thrombectomy stent 1 is provided with three developing elements 21 which extend along the distal end of the thrombectomy stent. The thrombectomy stent 1 is provided with two proximal ends 12.

Embodiment 18.4

Figure 22:
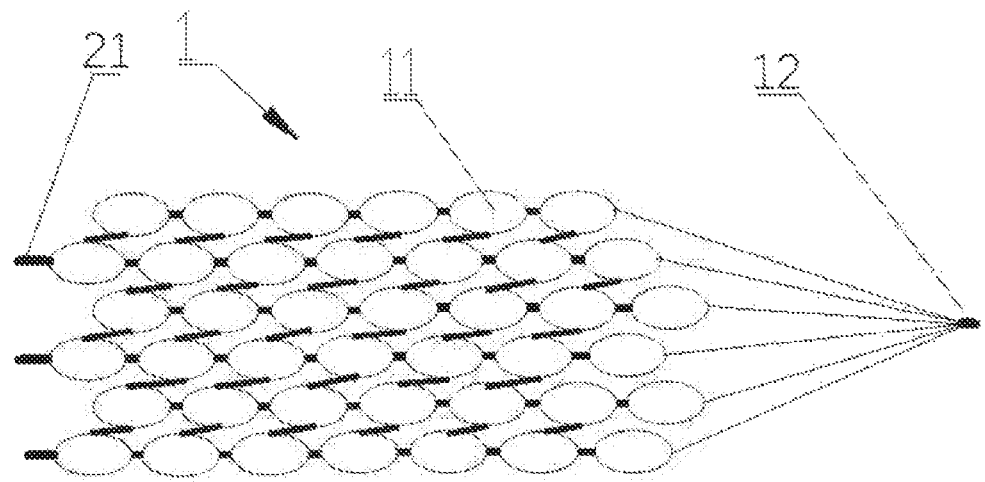
FIG. 22 is incision pattern VII of the thrombectomy stent.

In this embodiment, the incision pattern of the thrombectomy stent is as shown in FIG. 22. The thrombectomy stent 1 comprises a plurality of grid cells 11 connected to each other. The plurality of grid cells 11 are sequentially arranged in rows which are parallel to the axial direction of the thrombectomy stent 1, and the grid cells 11 in odd-numbered rows and in even-numbered rows are arranged in a staggered manner. The distal end of the thrombectomy stent 1 is provided with three developing elements 21 which extend along the distal end of the thrombectomy stent. The thrombectomy stent 1 is provided with one most proximal end 12.

Embodiment 19

In this embodiment, the thrombectomy stent comprises a plurality of grid cells connected to each other. The grid cells are of a pattern composed of arcs. Totally four (but not limited to four) developing elements are disposed at the ends of the grid cells at the most distal end of the thrombectomy stent. The grid cells include first grid cells and second grid cells. A plurality of first grid cells are sequentially arranged in first grid cell rows which are parallel to the axial direction of the thrombectomy stent; and a plurality of second grid cells are sequentially arranged in second grid cell rows which are parallel to the axial direction of the thrombectomy stent. The first grid cell rows and the second grid cell rows are alternately arranged in the axial direction and arranged in a staggered manner in a direction perpendicular to the axial direction, namely, the odd-numbered rows of the thrombectomy stent are the first grid cell rows, and the even-numbered rows are the second grid cell rows; or the even-numbered rows are the first grid cell rows, and the odd-numbered rows are the second grid cell rows; and in a direction perpendicular to the axial direction of the thrombectomy stent, the first grid cells are aligned with the gaps between every two adjacent second grid cells, and the second grid cells are aligned with the gaps between every two adjacent first grid cells. Such an arrangement is advantageous for uniform distribution of grid wires on respective segments of the thrombectomy stent and on the circumference of the cross section thereof, so that uniform support force can be provided and the thrombectomy effect is better.

The first grid cell is enclosed by four of the second grid cells adjacent to each other; and the second grid cell is enclosed by four of the first grid cells adjacent to each other.

Embodiment 20

Embodiment 20.1

In this embodiment, the grid wires of the grid cells include first grid wires and second grid wires. The width of the first grid wires is 0.07 mm; and the width of the second grid wires is 0.16 mm. The grid cells include first grid cells and second grid cells.

The size of the thrombectomy stent fully expanded into a plane following the perimeter of the cross section, that is, the size of the incision pattern of the thrombectomy stent is: the width of the first grid cells (perpendicular to the axial direction of the thrombectomy stent, the axial direction of the thrombectomy stent penetrating the distal end and the proximal end of the thrombectomy stent) is 4.55 mm, and the length (parallel to the axial direction of the thrombectomy stent) is 3.95 mm. The width of the second grid cells (perpendicular to the axial direction of the thrombectomy stent) is 4.36 mm, and the length (parallel to the axial direction of the thrombectomy stent) is 4.97 mm.

Between the first grid cells, the width of junctions in the axial direction of the thrombectomy stent (perpendicular to the axial direction of the thrombectomy stent) is 0.25 mm, and the length (parallel to the axial direction of the thrombectomy stent) is 0.45 mm.

Between the first grid cells, the width of junctions in a direction intersecting the axial direction of the thrombectomy stent (intersecting the axial direction of the thrombectomy stent) is 0.38 mm, and the length (approximately parallel to the axial direction of the thrombectomy stent) is 4.2 mm.

When the thrombectomy stent is expanded into a plane, its width (perpendicular to the axial direction of the thrombectomy stent) is 20.15 mm, and the length (parallel to the axial direction of the thrombectomy stent 1) is 38 mm.

Embodiment 20.2

In this embodiment, the grid wires of the grid cells include first grid wires, second grid wires and third grid wires. The width of the first grid wires is 0.07 mm; the width of the second grid wires is 0.16 mm; and the width of the third grid wires is 0.10 mm. The grid cells include first grid cells, second grid cells and third grid cells.

The grid wires and the grid cells are not limited to one, two or three types.

The values listed in Embodiments 20.1 and 20.2 above are intended to help understanding the present invention, but not limit the present invention to these values. In practical applications, different sizes may be designed according to the thrombi and the blood vessels to meet the needs of thrombectomy and are not limited to the above values.

Embodiment 21

Figure 23:
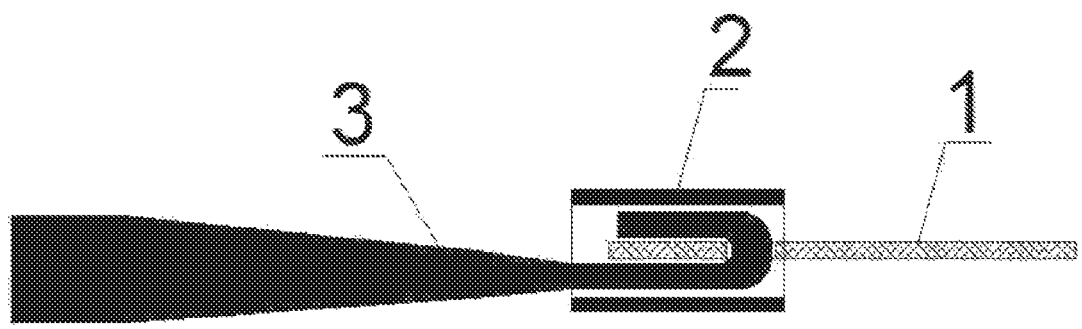
FIG. 23 is a schematic diagram of linking between the thrombectomy stent and a push rod in one specific embodiment.

As shown in FIG. 23, in this embodiment, the thrombectomy stent 1 is connected to the push rod 3 by linking, the developing ring 2 is sheathed outside the junction, and a UV adhesive and/or ab epoxy resin adhesive is/are coated in the developing ring 2 to further secure the connection of the thrombectomy stent 1 to the push rod 3.

Embodiment 22

Figure 24:
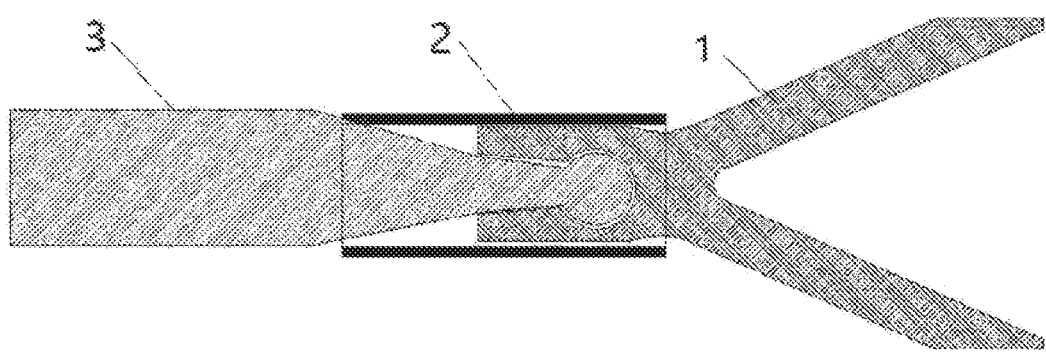
FIG. 24 is a schematic diagram of sleeve connection between the thrombectomy stent and the push rod in another specific embodiment.

As shown in FIG. 24, in this embodiment, the thrombectomy stent 1 is connected to the push rod 3 by means of sleeve connection, and the developing ring 2 is sheathed outside the junction.

Embodiment 23

Figure 25:
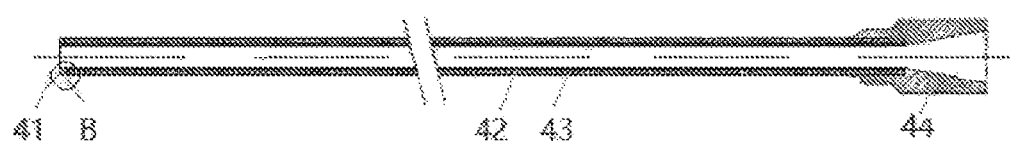
FIG. 25 is a structural schematic diagram of an introducing sheath.
Figure 26:
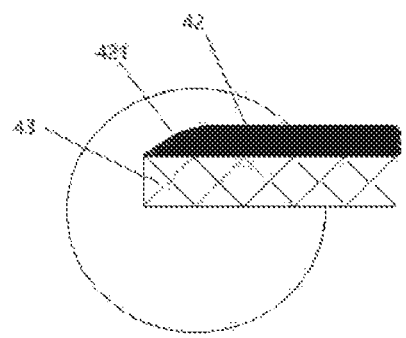
FIG. 26 is a partial enlarged view of the portion B in FIG. 24.

FIG. 25 shows one specific embodiment of an introducing sheath according to the present invention. The introducing sheath is a double-layer tube, the material of the inner-layer tube 42 including PTFE, and the material of the outer-layer tube 43 including nylon and/or Pebax. The introducing sheath serves to introduce the thrombectomy stent into a microcatheter along with the push rod. The microcatheter is a surgical accessory. A handle 44 is disposed at a proximal end of the introducing sheath. FIG. 26 shows a partially enlarged structure of the portion B in FIG. 25. As shown in FIG. 26, an inner wall 421 of the distal end of the inner-layer tube 42 is configured to have smooth rounded transition.

Embodiment 24

During operation, a 0.014 inch nerve-guide wire (e.g., Synchro® or Transend® guide wire) is introduced into a blood vessel and thrombus by means of a conventional catheter technique so as to connect a hemostasis valve to the microcatheter.

The distal end of the microcatheter is then delivered to 10 mm away from the distal end of the thrombus if the vascular condition permits. The guide wire is removed from the microcatheter.

The introducing sheath is inserted into half of the hemostasis valve and is gently tightened. The introducing sheath is flushed with physiological saline till the physiological saline flows out from the proximal end of the introducing sheath. The hemostasis valve is released, the introducing sheath is delivered into a connector of the microcatheter, and the hemostasis valve is tightened. The push rod in the introducing sheath is operated to push the thrombectomy stent which is located in the introducing sheath. When approximately half of the thrombectomy stent is delivered into the microcatheter, the introducing sheath is removed, and the thrombectomy stent is further pushed till the microcatheter is completely exposed out of the distal end of the thrombectomy stent. In this embodiment, the distal end of the thrombectomy stent comprises a head end and a tapered distal section, the head end being 4 mm long, and the tapered distal section being 6 mm long.

The microcatheter is withdrawn to completely release the thrombectomy stent. At this time, the catching member is in the first state, the thrombectomy stent is in the fourth state, the middle segment of the thrombectomy stent is in contact with the thrombus, the thrombus generates a force on the grid cells of this segment, and the grid cells are collapsed and change in shape, so that the outer diameter of the middle segment of the thrombectomy stent is less than the outer diameters of the two ends thereof.

After a period of time (about 5 minutes), the thrombus are fully fused and embedded into the thrombectomy stent, and the outer diameter of the middle segment of the stent is slowly restored to the original shape or close to the original shape.

Then, after some routine operations of blocking proximal blood flow may be performed, the push rod is pulled so that the catching member is in the second state, both the thrombectomy stent and the catching member are located in the microcatheter, and then the thrombectomy stent, the catching member, the push rod and the microcatheter are slowly pulled out as a whole. Post treatment is performed. The thrombectomy is completed.

The thrombectomy stent in the introducing sheath is curled greatly, so that the outer diameter of the thrombectomy stent is small enough to be loaded into the introducing sheath. When the thrombectomy stent is released from the introducing sheath, its outer diameter is increased. When no external force acts on the thrombectomy stent, it is in the third state, and as shown in FIG. 1, the grid cells are stable in shape.

The specific preferred embodiments of the present invention are described in detail as above. It should be appreciated that a person of ordinary skill in the art would be able to make modifications and variations in accordance with the concept of the present invention without involving any inventive effort. Therefore, any technical solution that can be obtained by a person skilled in the art by means of logical analysis, reasoning or limited trials on the basis of the prior art and according to the concept of the present invention should be included within the scope of protection of the claims.

The invention claimed is:

1. A thrombectomy stent system, comprising a thrombectomy stent, wherein the thrombectomy stent is roll-shaped; and a cross section of the thrombectomy stent is of an open-ring structure; wherein both a distal end and a proximal end of the thrombectomy stent are in an open state;
   wherein the thrombectomy stent comprises a plurality of identical or different grid cells, wherein an aperture of the grid cells in the middle of the thrombectomy stent is greater than an aperture of the grid cells at two ends, and a support force of the grid cells in the middle of the thrombectomy stent is greater than a support force of the grid cells at two ends;
   wherein the grid cells include first grid cells and second grid cells; a plurality of the first grid cells are sequentially arranged in first grid cell rows which are parallel to an axial direction of the thrombectomy stent; a plurality of the second grid cells are sequentially arranged in second grid cell rows which are parallel to an axial direction of the thrombectomy stent; an odd-numbered rows of the thrombectomy stent are the first grid cell rows, and an even-numbered rows are the second grid cell rows; or an even-numbered rows are the first grid cell rows, and an odd-numbered rows are the second grid cell rows; and in a direction perpendicular to the axial direction of the thrombectomy stent, the first grid cells are aligned with gaps between every two adjacent second grid cells, and the second grid cells are aligned with gaps between every two adjacent first grid cells;
   wherein during thrombectomy, an outer diameter of a middle segment of the thrombectomy stent, which is referred to as a thrombectomy part, is reduced, and outer diameters of the distal end and the proximal end of the thrombectomy stent are greater than that of the thrombectomy part, and at this time the thrombectomy stent is dumbbell-shaped;
   wherein the thrombectomy stent further comprises a push rod, a distal end of the push rod is configured in a tapered step shape to provide a smooth transition when connected to the proximal end of the thrombectomy stent, and an outer surface of the push rod is coated with a polymer material with a low friction coefficient.

2. The thrombectomy stent system of claim 1, wherein the closer to a most proximal end of the thrombectomy stent is, the smaller a perimeter of the cross section of a proximal end of the thrombectomy stent.

3. The thrombectomy stent system of claim 2, wherein the cross section of the most proximal end of the thrombectomy stent is reduced to a dot.

4. The thrombectomy stent system of claim 1, wherein the cross section of a proximal end of the thrombectomy stent is C-shaped.

5. The thrombectomy stent system of claim 1, wherein the grid cells are connected to each other in a mesh shape.

6. The thrombectomy stent system of claim 1, wherein a shape of the grid cells includes one or more of a pattern composed of arcs and a pattern composed of polygons, arcs and straight lines.

7. The thrombectomy stent system of claim 1, wherein a shape of the grid cells includes one or more of a circle, an ellipse, a quadrangle, a triangle, a diamond and a trapezoid.

8. The thrombectomy stent system of claim 1, wherein a material of the thrombectomy stent includes a memory alloy.

9. The thrombectomy stent system of claim 1, wherein developing elements are disposed at a distal end of the thrombectomy stent; and a proximal end of the thrombectomy stent is connected to a distal end of the push rod, and a developing element is disposed at a junction.

10. A thrombectomy device, comprising a thrombectomy stent, wherein developing elements are disposed on the thrombectomy stent, wherein the thrombectomy stent comprises a plurality of identical or different grid cells, wherein an aperture of the grid cells in the middle of the thrombectomy stent is greater than an aperture of the grid cells at two ends, and a support force of the grid cells in the middle of the thrombectomy stent is greater than a support force of the grid cells at two ends; wherein both a distal end and a proximal end of the thrombectomy stent are in an open state;
   wherein the grid cells include first grid cells and second grid cells; a plurality of the first grid cells are sequentially arranged in first grid cell rows which are parallel to an axial direction of the thrombectomy stent; a plurality of the second grid cells are sequentially arranged in second grid cell rows which are parallel to an axial direction of the thrombectomy stent; an odd-numbered rows of the thrombectomy stent are the first grid cell rows, and an even-numbered rows are the second grid cell rows; or an even-numbered rows are the first grid cell rows, and an odd-numbered rows are the second grid cell rows; and in a direction perpendicular to the axial direction of the thrombectomy stent, the first grid cells are aligned with gaps between every two adjacent second grid cells, and the second grid cells are aligned with gaps between every two adjacent first grid cells;
   wherein during thrombectomy, an outer diameter of a middle segment of the thrombectomy stent, which is referred to as a thrombectomy part, is reduced, and outer diameters of the distal end and the proximal end of the thrombectomy stent are greater than that of the thrombectomy part, and at this time the thrombectomy stent is dumbbell-shaped;
   wherein the thrombectomy stent further comprises a push rod, a distal end of the push rod is configured in a tapered step shape to provide a smooth transition when connected to the proximal end of the thrombectomy stent, and an outer surface of the push rod is coated with a polymer material with a low friction coefficient.

11. The thrombectomy device of claim 10, wherein the developing elements are disposed at both the distal end and the proximal end of the thrombectomy stent.

12. The thrombectomy device of claim 11, wherein a number of the developing elements at the distal end of the thrombectomy stent is greater than or equal to 2, and the developing elements at the distal end of the thrombectomy stent are uniformly distributed at the distal end of the thrombectomy stent; and a number of the developing elements at the proximal end of the thrombectomy stent is greater than or equal to 2, and the developing elements at the proximal end of the thrombectomy stent are uniformly distributed at the proximal end of the thrombectomy stent.

13. The thrombectomy device of claim 11, wherein developing elements are disposed at a middle segment of the thrombectomy stent.

14. The thrombectomy device of claim 13, wherein a number of the developing elements at the distal end of the thrombectomy stent is greater than or equal to 2, and the developing elements at the distal end of the thrombectomy stent are uniformly distributed at the distal end of the thrombectomy stent; a number of the developing elements at the proximal end of the thrombectomy stent is greater than or equal to 2, and the developing elements at the proximal end of the thrombectomy stent are uniformly distributed at the proximal end of the thrombectomy stent; and a number of the developing elements at the middle segment of the thrombectomy stent is greater than or equal to 2, and the developing elements at the middle segment of the thrombectomy stent are uniformly distributed at the middle segment of the thrombectomy stent.

15. The thrombectomy device of claim 10, wherein the developing elements include line-shaped developing lines.

16. The thrombectomy device of claim 15, wherein one end of the developing lines is disposed at the distal end or a distal end face of the thrombectomy stent, and the other end thereof is disposed at the proximal end or a proximal end face of the thrombectomy stent.

17. The thrombectomy device of claim 15, wherein a number of the developing lines is greater than or equal to 3, and the developing lines are uniformly arranged on the thrombectomy stent.

18. The thrombectomy device of claim 15, wherein the thrombectomy stent is roll-shaped; the cross section of the thrombectomy stent is of an open-ring structure; the thrombectomy stent is roll-shaped; and the developing lines extend in a direction of the roll-shaped circumference of the thrombectomy stent.

19. The thrombectomy device of claim 15, wherein the thrombectomy stent is roll-shaped; the cross section of the thrombectomy stent is of an open-ring structure; and the developing lines not only axially extend along the thrombectomy stent but also extend back and forth in the direction of the roll-shaped circumference of the thrombectomy stent.

20. The thrombectomy device of claim 10, wherein the developing elements are disposed in a manner including one or more of spraying or brushing a developing material to the thrombectomy stent or mounting the developing elements onto the thrombectomy stent by means of winding, buckling, perforating, soldering or bonding.

21. The thrombectomy device of claim 10, wherein the entire thrombectomy stent is covered with a developing material.

22. The thrombectomy device of claim 10, wherein the developing elements include a mesh-shaped developing mesh; and the developing mesh is located at a most distal end of the thrombectomy stent to close an opening at a distal end of the thrombectomy stent.

23. A thrombectomy device system, comprising a thrombectomy stent, a push rod and a catching member, wherein a proximal end of the thrombectomy stent is connected to the push rod, and the proximal end of the thrombectomy stent or the push rod is connected to the catching member; and the catching member is configured to receive the thrombectomy stent, wherein the thrombectomy stent comprises a plurality of identical or different grid cells, wherein an aperture of the grid cells in the middle of the thrombectomy stent is greater than an aperture of the grid cells at two ends, and a support force of the grid cells in the middle of the thrombectomy stent is greater than a support force of the grid cells at two ends; wherein both a distal end and a proximal end of the thrombectomy stent are in an open state;
wherein the grid cells include first grid cells and second grid cells; a plurality of the first grid cells are sequentially arranged in first grid cell rows which are parallel to an axial direction of the thrombectomy stent; a plurality of the second grid cells are sequentially arranged in second grid cell rows which are parallel to an axial direction of the thrombectomy stent; an odd-numbered rows of the thrombectomy stent are the first grid cell rows, and an even-numbered rows are the second grid cell rows; or an even-numbered rows are the first grid cell rows, and an odd-numbered rows are the second grid cell rows; and in a direction perpendicular to the axial direction of the thrombectomy stent, the first grid cells are aligned with gaps between every two adjacent second grid cells, and the second grid cells are aligned with gaps between every two adjacent first grid cells;
wherein during thrombectomy, an outer diameter of a middle segment of the thrombectomy stent, which is referred to as a thrombectomy part, is reduced, and outer diameters of the distal end and the proximal end of the thrombectomy stent are greater than that of the thrombectomy part, and at this time the thrombectomy stent is dumbbell-shaped;
wherein a distal end of the push rod is configured in a tapered step shape to provide a smooth transition when connected to the proximal end of the thrombectomy stent, and an outer surface of the push rod is coated with a polymer material with a low friction coefficient.

24. The thrombectomy device system of claim 23, wherein the catching member comprises a first end and a second end; the first end is connected to the proximal end of the thrombectomy stent or the push rod; the second end is provided with an opening; and the opening is configured for the thrombectomy stent and the push rod to pass through.

25. The thrombectomy device system of claim 24, wherein the first end is fixedly connected to the proximal end of the thrombectomy stent or the push rod by means of sheathing outside or by means of soldering, gluing, mechanical connection or the like.

26. The thrombectomy device system of claim 24, wherein the catching member has a first state and a second state; in the first state, the thrombectomy stent is located outside the catching member; and in the second state, the thrombectomy stent is disposed inside the catching member.

27. The thrombectomy device system of claim 26, wherein a transition from the first state to the second state is set as follows: the first end, extending out of a distal end of a microcatheter, and the thrombectomy stent are withdrawn into the microcatheter by means of the push rod pushing back the thrombectomy stent, and pass through the second end in the microcatheter, so that the first end is located at a proximal end of the catching member, and the second end is located at a distal end of the catching member, so that the thrombectomy stent is sheathed in the catching member.

28. The thrombectomy device system of claim 27, wherein during the thrombectomy stent and the first end being pulled back into the microcatheter by the push rod, under action of the resistance or/and the friction of the microcatheter to the catching member, a withdrawing speed of the second end is less than the withdrawing speed of the first end, so that the thrombectomy stent and the first end can pass through the second end.

29. The thrombectomy device system of claim 27, wherein in the first state, the first end is located at the distal end of the catching member, and the second end is located at the proximal end of the catching member; and the transition from the first state to the second state enables the catching member to turn inside out and shift front and back.

30. The thrombectomy device system of claim 27, wherein in the second state, the opening of the second end tends to close.

31. The thrombectomy device system of claim 27, wherein the catching member is woven in such a manner that the opening in the second end tends to open in the first state; and when in the second state, i.e., after the catching member turns inside out, the opening in the second end tends to close again.

32. The thrombectomy device system of claim 23, wherein the catching member is made of metal and/or a polymer material.

33. The thrombectomy device system of claim 23, wherein the length of the catching member is greater than that of the thrombectomy stent.

34. The thrombectomy device system of claim 23, wherein the catching member is of a mesh structure, a grid size of which is less than that of the grid cells.

* * * * *